United States Patent
Song et al.

(10) Patent No.: US 9,259,509 B2
(45) Date of Patent: *Feb. 16, 2016

(54) THERMAL RESPONSIVE POLYMER SILOXANES, COMPOSITIONS, AND METHOD AND APPLICATIONS RELATED THERETO

(71) Applicant: University of Massachusetts Medical School, Boston, MA (US)

(72) Inventors: Jie Song, Shrewsbury, MA (US); Jianwen Xu, Worcester, MA (US)

(73) Assignee: University of Massachusetts, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/286,834

(22) Filed: May 23, 2014

(65) Prior Publication Data
US 2014/0255333 A1    Sep. 11, 2014

Related U.S. Application Data

(63) Continuation of application No. 12/450,872, filed as application No. PCT/US2008/005059 on Apr. 18, 2008, now Pat. No. 8,765,112.

(51) Int. Cl.
| | | |
|---|---|---|
| *A61K 31/74* | (2006.01) | |
| *A61L 27/18* | (2006.01) | |
| *A61L 31/06* | (2006.01) | |
| *C08G 18/61* | (2006.01) | |
| *C08G 63/695* | (2006.01) | |
| *C08G 77/04* | (2006.01) | |
| *C08G 77/38* | (2006.01) | |
| *C08G 77/445* | (2006.01) | |
| *A61L 27/50* | (2006.01) | |

(52) U.S. Cl.
CPC ............ *A61L 27/18* (2013.01); *A61L 27/50* (2013.01); *A61L 31/06* (2013.01); *C08G 18/61* (2013.01); *C08G 63/6952* (2013.01); *C08G 77/045* (2013.01); *C08G 77/38* (2013.01); *C08G 77/445* (2013.01); *A61L 2400/16* (2013.01)

(58) Field of Classification Search
None
See application file for complete search history.

*Primary Examiner* — Brian Gulledge
(74) *Attorney, Agent, or Firm* — Milstein Zhang & Wu LLC

(57) ABSTRACT

The invention relates to materials comprising siloxanes, preferably the materials have thermal-responsive properties. In some embodiments, the invention relates to silsesquioxane groups functionalized with polymers. In another embodiment, silsequioxane-polymer conjugates comprise polylactone segments. The silsequioxane-polymer conjugates may be crosslinked together to form a material, and these materials may be functionalized with bioactive compounds so that the materials have desirable biocompatibility or bioactivity when used in medical devices. In further embodiments, the invention relates to composite materials that contain a polymer matrix and aggregates, and in some embodiments, methods of making, and methods of using these materials. Preferably, the aggregates are calcium phosphate aggregates. Preferably, the material is resistant to fracture. In further embodiments, the materials are used in surgical procedures of bone replacement. In further embodiments, the materials contain polyhedral silsesquioxanes and/or biodegradable segments.

20 Claims, 28 Drawing Sheets

(a) Random structure (b) Ladder structure (T$_8$) (c)

(T$_{10}$) (d)

(T$_{12}$) (e)

Cage structures

36
Epoxy cyclohexyl dimethyl-silyl-POSS
$C_{46}H_{82}O_{14}Si_9$ $M_w$: 1099
For Epoxy resins

37
Methacryl dimethyl-silyl-POSS
$C_{44}H_{80}O_{15}Si_9$ $M_w$: 1102
For Acrylic resins, Vinyl ester resins

38
NorbornenylethylDisilanol
$C_{46}H_{84}O_{12}Si_9$ $M_w$: 1053.84
For DCPD resins, Siloxane resins
and DCPD/siloxane hybrids

39
Isobutyl Methylacyl-POSS
$C_{35}H_{74}O_{14}Si_8$ $M_w$: 943.64
For Acrylic resins, Vinyl ester resins

| | $M_n$ | Theoretical | GPC | NMR | PDI |
|---|---|---|---|---|---|
| n=10 | | 7245 | 7328 | 5587 | 1.20 |
| n=20 | | 13010 | 13576 | 9988 | 1.19 |
| n=40 | | 24541 | 25788 | 19576 | 1.36 |

FIGURE 7I

| Shape memory polymer samples | Storage Modulus at 37 °C (MPa) | Storage Modulus at 80 °C (MPa) | Tan Delta | $T_{trans}$ (°C)* |
|---|---|---|---|---|
| 2, n=10 | 2196±56 | 4.156±0.084 | 2.407±0.051 | 52.7±0.81 |
| 2, n=20 | 2745.7±204.3 | 2.316±0.081 | 2.875±0.034 | 58.7±0.47 |
| 7, n=20 | 2581.7±108.7 | 1.482±0.098 | 2.768±0.068 | 53.4±0.43 |
| 2, n=40 | 2545.7±260.3 | 1.649±0.118 | 2.936±0.041 | 61.6±0.61 |

FIGURE 8H

Example 1. The reactive group is hydroxyl and biomolecule attached to the connecting group is integrin binding peptide

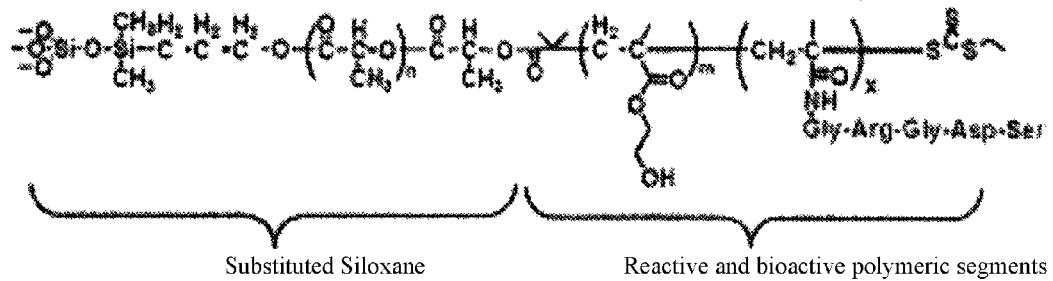

Substituted Siloxane — Reactive and bioactive polymeric segments

Example 2. The reactive group is azide and biomolecule attached to the connecting group is HA-binding peptide

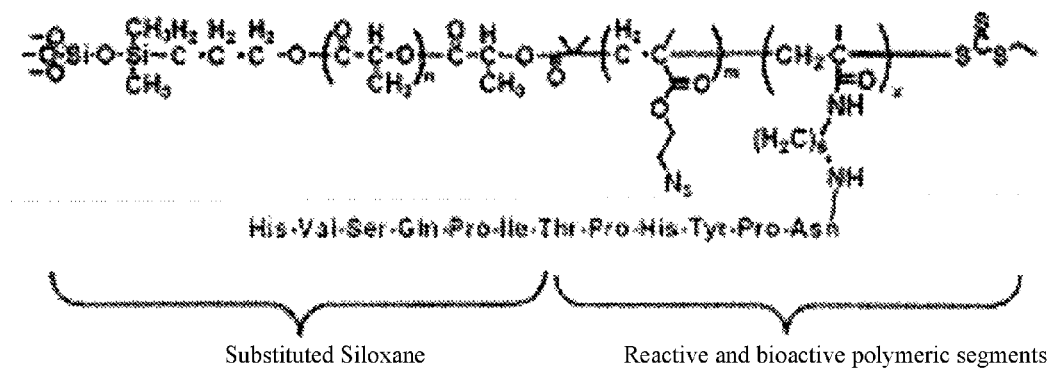

Substituted Siloxane — Reactive and bioactive polymeric segments

Example 3. The reactive group is methacrylate and biomolecule attached to the connecting group is integrin-binding peptide

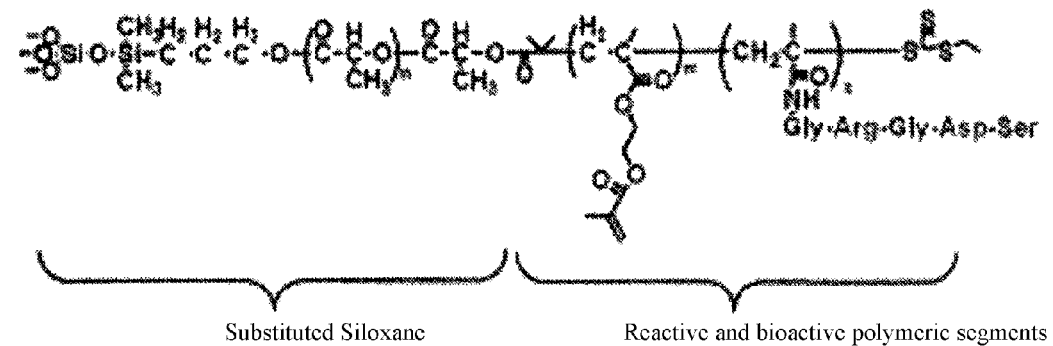

Substituted Siloxane — Reactive and bioactive polymeric segments

Crosslinked by Radical chemistry

Crosslinked by Radical chemistry

THERMAL RESPONSIVE POLYMER SILOXANES, COMPOSITIONS, AND METHOD AND APPLICATIONS RELATED THERETO

PRIORITY CLAIMS AND RELATED APPLICATIONS

This application is a continuation of and claims the benefit of priority from U.S. application Ser. No. 12/450,872, filed Nov. 24, 2009, which was the U.S. national phase of PCT/US2008/005059 filed Apr. 18, 2008, the entire content of each of which is incorporated herein by reference in its entirety.

FIELD OF INVENTION

The invention relates to materials comprising siloxanes, preferably the materials have thermal-responsive properties. In some embodiments, the invention relates to silsesquioxane groups functionalized with polymers. In another embodiment, silsequioxane-polymer conjugates comprise polylactone segments. The silsequioxane-polymer conjugates may be crosslinked together to form a material, and these materials may be functionalized with bioactive compounds so that the materials have desirable biocompatibility or bioactivity when used in medical devices. In further embodiments, the invention relates to composite materials that contain a polymer matrix and aggregates, and in some embodiments, methods of making, and methods of using these materials. Preferably, the aggregates are calcium phosphate aggregates. Preferably, the material is resistant to fracture. In further embodiments, the materials are used in surgical procedures of bone replacement. In further embodiments, the materials contain polyhedral silsesquioxanes and/or biodegradable segments.

BACKGROUND

Thermal-responsive materials—shape memory alloys (SMA) and shape memory polymers (SMP)—are capable of switching between shapes upon exposure to a particular thermal environment. This unique property can be utilized to enhance the performance of many biomedical devices. However, known materials have certain physical property limitations that hinder broad use in biomedical applications. Some of these properties include low deformability (<8%), the necessity of high-temperature and time-consuming processing, as well as poor biocompatibility and degradability. Such properties are beneficial in, for example, the surgical removal of bone segments, a common treatment for osteosarcoma. The lack of a bone segment presents substantial problems for the patients, which are typically addressed by bone grafts. Bone cement such as Plexiglas, polymethylmethacrylate (PMMA), is used in joint, hip and shoulder replacement surgeries to bond metallic devices with bone. The benefits of such surgeries suffer from a relatively short lifetime due to PMMA's limited capacity to integrate with bony tissue and susceptibility to fatigue and fracture. Moreover, these organic scaffolds are intrinsically weak, and do not provide immediate solutions for large skeletal defects where moderate loads are expected. Thus, there is a need to develop materials that overcome both the limitations of currently employed materials and a need to develop bone substitutes that provide flexibility that facilitates surgical fitting, a degree of porosity to promote osteointegration, and strength and toughness against compressive forces.

SUMMARY OF THE INVENTION

The invention relates to materials comprising siloxanes, preferably the materials have thermal-responsive properties. In some embodiments, the invention relates to silsesquioxane groups functionalized with polymers. In another embodiment, silsequioxane-polymer conjugates comprise polylactone segments. The silsequioxane-polymer conjugates may be crosslinked together to form a material, and these materials may be functionalized with bioactive compounds so that the materials have desirable biocompatibility or bioactivity when used in medical devices. In further embodiments, the invention relates to composite materials that contain a polymer matrix and aggregates, and in some embodiments, methods of making, and methods of using these materials. Preferably, the aggregates are calcium phosphate aggregates. Preferably, the material is resistant to fracture. In further embodiments, the materials are used in surgical procedures of bone replacement. In further embodiments, the materials contain polyhedral silsesquioxanes and/or biodegradable segments.

In some embodiments, the invention relates a macromer structure comprising a siloxane core, polymeric segments, and end groups. In preferred embodiments, the end groups and/or the side chain end groups of the polymeric segments may be crosslinked together using urethane chemistry or radical chemistry, both of which are synthetic techniques that are well known to those of ordinary skill in the art. While it is not intended that the present invention be limited by the chemical methods used to generate the present invention preferred methods include but are not limited to ring opening polymerization (ROP), reversible addition fragmentation transfer (RAFT) and atom transfer radical polymerization (ATRP). Furthermore, it is not intended that the present invention be limited to the classification of polymeric segments that comprise the invention; preferred embodiments include but are in no way limited to monomeric polymers or homopolymers, copolymers and block copolymers. In further embodiments, the end groups comprise alkenyl groups, e.g., acrylate or methacrylate. In further embodiments, the end groups or the side chain end groups of the polymeric segments are crosslinked with diisocyanate, diester, diacid, or diacyl by cordensation chemistry when the end groups are nucleophilic groups (such as —OH, —NH2, —SH, —COOH). In further embodiments, the end groups are crosslinked with high fidelity chemical ligation (such as the modified Staudinger ligation, the "Click" chemistry).

In some embodiments, the invention relates to a medical device comprising a material comprising: a) siloxane moieties, b) polymer groups, and c) linking groups; wherein said siloxane moieties are substituted with three or more of said polymer groups to form a siloxane-polyester conjugate; and said linking groups are configured to join said conjugates through covalent bonds of said polymer groups. In further embodiments, said polymer groups are polyester groups. In further embodiments, said material has shape memory. In further embodiments, said siloxane moieties are selected from the group consisting of silsesquioxanes and metallasiloxanes. In further embodiments said material comprises a biocompatible or bioactive peptide. In further embodiment, said material surface comprises carboxylic acid groups. In further embodiments, said medical device is selected from the group consisting of cardiovascular stents, surgical guide wires, and orthodontic wires.

In some embodiments, the invention relates to a material comprising: a) siloxane moieties, b) polymer groups, and c) linking groups; wherein said siloxane moieties are substituted with three or more of said polymer groups to form a siloxane-polymer conjugate; and said linking groups join said conjugates through covalent bonds of said polymer groups. In further embodiments, said polymer groups are polyester groups. In further embodiments, said material has one-way or two-way shape memory. In further embodiments, said material has a Tg between 17° C. and 100° C. In further embodiments, said material has a Tg between 37° C. and 50° C. In further embodiments, said siloxane moieties are selected from the group consisting of silsesquioxanes and metallasiloxanes. In further embodiments, said siloxane moieties are caged structures. In further embodiments, said siloxane moieties are octakis(hydidodimethylsiloxy)octasesquioxanes. In further embodiments, said polyester groups are polylactones. In further embodiments, said linking groups comprise alkyl, aryl, or polyethylene groups. In further embodiments, said linking groups comprise urethane groups.

In yet another embodiment, the invention relates to a compound having the formula:

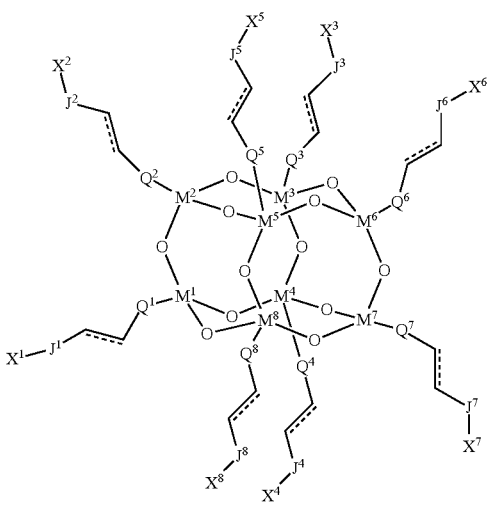

wherein, $X^1$, $X^2$, $X^3$, $X^4$, $X^5$, $X^6$, $X^7$, and $X^8$ are the same or different and, at each occurrence, independently nucleophilic groups; $J^1$, $J^2$, $J^3$, $J^4$, $J^5$, $J^6$, $J^7$, and $J^8$ are the same or different and, at each occurrence, independently joining groups; ══ is a single or double bond; $Q^1$, $Q^2$, $Q^3$, $Q^4$, $Q^5$, $Q^6$, $Q^7$, $Q^8$ are the same or different and, at each occurrence, independently —O-$M^9R^1R^2$—, —O-$M^{10}R^3R^4$—, —O-$M^{11}R^5R^6$—, —O-$M^{12}R^7R^8$—, —O-$M^{13}R^9R^{10}$—, —O-$M^{14}R^{11}R^{12}$—, —O-$M^{15}R^{13}R^{14}$—, —O-$M^{16}R^{15}R^{16}$—, —O-$M^9R^1R^2$—, or absent forming a bond between adjacent atoms; $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, and $M^{16}$ are the same or different and, at each occurrence, independently a metal or metalloid atom; $R^1$, $R^2$, $R^3$, $R^4$, $R^5$, $R^6$, $R^7$, $R^8$, $R^9$, $R^{10}$, $R^{11}$, $R^{12}$, $R^3$, $R^{14}$, $R^{15}$, and $R^{16}$ are the same or different and, at each occurrence, independently alkyl, substituted alkyl, aryl, substituted aryl, —Oalkyl, substituted —Oalkyl, —Oaryl, or substituted —Oaryl. In further embodiments, said nucleophilic groups are selected from the groups consisting of —OH, —SH, and —$NH_2$. In further embodiments, said metal or metalloid atom is selected from the group consisting of Si, Ti, Zr, Li, Co, and Cr. In further embodiments, said joining groups are selected from the group consisting of —$(CH_2)_n$—, —$(OCH_2CH_2)_n$—, —(C═O)—, and —((C═O)O$(CH_2)_n$)— wherein n is 1 to 22.

In still another embodiments, the invention relates to a compound having the formula:

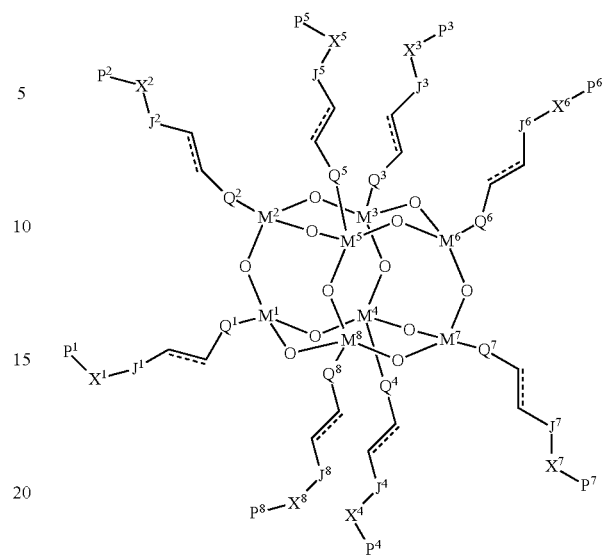

wherein $P^1$, $P^2$, $P^3$, $P^4$, $P^5$, $P^6$, $P^7$, and $P^8$ are the same or different and, at each occurrence, independently a polymer moiety; $X^1$, $X^2$, $X^3$, $X^4$, $X^5$, $X^6$, $X^7$, and $X^8$ are the same or different and, at each occurrence, independently —O—, —S—, —NH—, or —$NR^{19}$—; $J^1$, $J^2$, $J^3$, $J^4$, $J^5$, $J^6$, $J^7$, and $J^8$ are the same or different and, at each occurrence, independently joining groups; ══ is a single or double bond; $Q^1$, $Q^2$, $Q^3$, $Q^4$, $Q^5$, $Q^6$, $Q^7$, $Q^8$ are the same or different and, at each occurrence, independently —O-$M^9R^1R^2$—, —O-$M^{10}R^3R^4$—, —O—$M^{11}R^5R^6$—, —O-$M^{12}R^7R^8$—, —O-$M^{13}R^9R^{10}$—, —O-$M^{14}R^{11}R^{12}$—, —O-$M^{15}R^{13}R^{14}$—, —O-$M^{16}R^{15}R^{16}$—, —O-$M^9R^1R^2$—, or absent forming a bond between adjacent atoms; $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, and $M^{16}$ are the same or different and, at each occurrence, independently a metal or metalloid atom; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are the same or different and, at each occurrence, independently alkyl, substituted alkyl, aryl, substituted aryl, —Oalkyl, substituted —Oalkyl, —Oaryl, or substituted —Oaryl; and $R^{19}$ is alkyl. In further embodiments, three or more of said polymer moieties have the following structural formula:

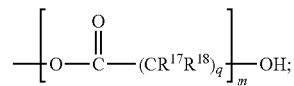

wherein $R^{17}$ and $R^{18}$ are the same or different and, at each occurrence, independently hydrogen, alkyl, or substituted alkyl; q is 1 to 4, 5, or 7; and m is 2 to 1000. In further embodiments, three or more of $P^1$, $P^2$, $P^3$, $P^4$, $P^5$, $P^6$, $P^7$, and $P^8$ have the following structural formula:

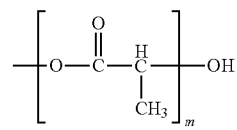

wherein m is 2 to 1000.

In another embodiment, the invention relates to a material made from reacting the compounds disclosed herein with a crosslinking agent. In further embodiments, said crosslinking agent is a diisocyanate. In further embodiments, said diisocyanate is hexamethylene diisocyanate In some embodiments, the invention relates to a compound having the following formula:

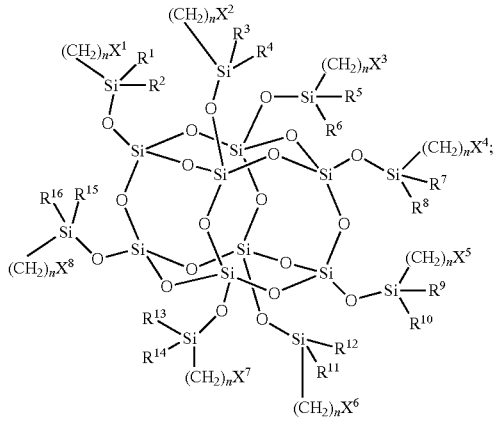

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are the same or different and, at each occurrence, independently alkyl; n is 3 to 22; $X^1$, $X^2$, $X^3$, $X^4$, $X^5$, $X^6$, $X^7$, and $X^8$ are the same or different and, at each occurrence, independently —OH, —SH, —NH$_2$, or a group having the following structural formula;

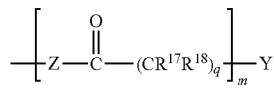

$R^{17}$, and $R^{18}$ are the same or different and, at each occurrence, independently hydrogen or alkyl; m is 2 to 1000; q is 1 to 4 or 5 or 7; Y and —OH, —SH, or —NH$_2$; and Z is —O—, —S—, or —NH—. In further embodiments, three or more of $X^1$, $X^2$, $X^3$, $X^4$, $X^5$, $X^6$, $X^7$, and $X^8$ have the structural formula:

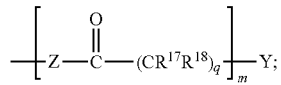

wherein m is 2 to 1000. In further embodiments, $X^1$, $X^2$, $X^3$, $X^4$, $X^5$, $X^6$, $X^7$, and $X^8$ are the same or different and, at each occurrence, independently —OH, —SH, —NH$_2$, or groups having the following formula:

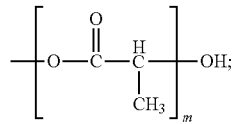

wherein m is 2 to 1000. In further embodiments, three or more of $X^1$, $X^2$, $X^3$, $X^4$, $X^5$, $X^6$, $X^7$, and $X^8$ have the structural formula:

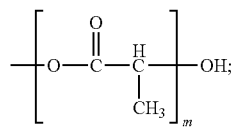

wherein m is 2 to 1000.

In further embodiments, the invention relates to a material comprising a polymer having a formula:

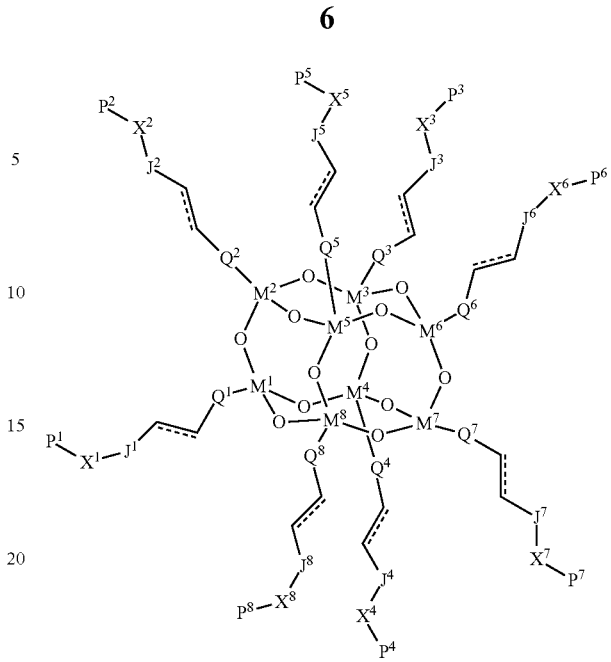

wherein $P^1$, $P^2$, $P^3$, $P^4$, $P^5$, $P^6$, $P^7$ and $P^8$ are the same or different and, at each occurrence, independently hydrogen, a polymer moiety, or a polymer moiety covalently bound to a group having the following structural formula:

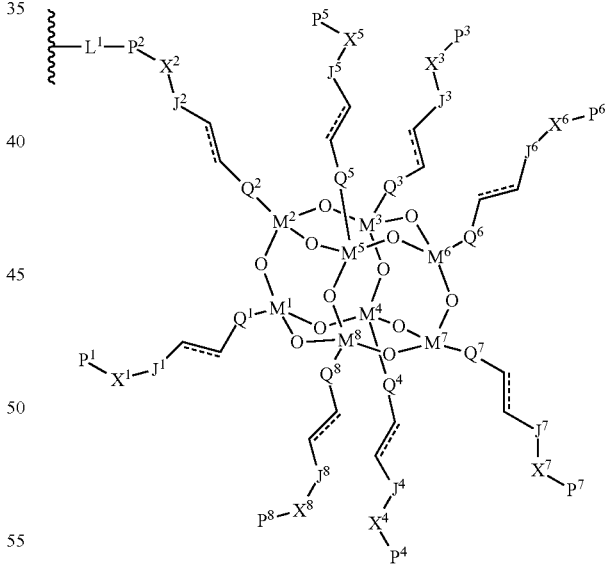

$L^1$ is a linking group, provided that at least three of said $P^1$, $P^2$, $P^3$, $P^4$, $P^5$, $P^6$, $P^7$, and $P^8$ have said polymer moieties covalently bound to said groups having said structural formula; $X^1$, $X^2$, $X^3$, $X^4$, $X^5$, $X^6$, $X^7$, and $X^8$ are the same or different and, at each occurrence, independently —O—, —S—, —NH—, —NR$^{21}$—; $J^1$, $J^2$, $J^3$, $J^4$, $J^5$, $J^6$, $J^7$, and $J^8$ are the same or different and, at each occurrence, independently joining groups; ▬▬ is a single or double bond; $Q^1$, $Q^2$, $Q^3$, $Q^4$, $Q^5$, $Q^6$, $Q^7$, $Q^8$ are the same or different and, at each occurrence, independently —O-M$^9$R$^1$R$^2$—, —O-M¹⁰R³R⁴—, —O-M¹¹R⁵R⁶—, —O-M¹²R⁷R⁸—, —O-M¹³R⁹R¹⁰—, —O-M¹⁴R¹¹R¹²—, —O-M¹⁵R¹³R¹⁴—, —O-M¹⁶R¹⁵R¹⁶—, —O-M⁹R¹R²—, or absent forming a bond between adjacent atoms; $M^1, M^2, M^3, M^4, M^5, M^6, M^7, M^8, M^9, M^{10}, M^{11}, M^{12}, M^{13}, M^{14}, M^{15}$, and $M^{16}$ are the same or different and, at each occurrence, independently a metal or metalloid atom; $R^1, R^2, R^3, R^4, R^5, R^6, R^7, R^8, R^9, R^{10}, R^{11}, R^{12}, R^{13}, R^{14}, R^{15}$, and $R^{16}$ are the same or different and, at each occurrence, independently alkyl, —Oalkyl, or —Oaryl; and $R^{21}$ is alkyl. In further embodiments, said metal or metalloid atom is selected from the group consisting of Si, Ti, Zr, Li, Co, and Cr. In further embodiments, said joining groups are selected from the group consisting of —(CH₂)—, —(OCH₂CH₂)$_n$—, —(C=O), and —((C=O)O(CH₂)$_n$)— wherein n is 1 to 22. In further embodiments, said polymer moieties are covalently bound to -L¹- with a structure having the following structural formula:

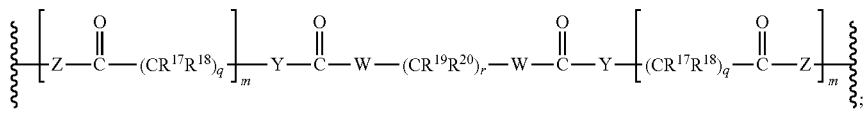

wherein r is 1 to 22, $R^{17}$, $R^{18}$, $R^{19}$ and $R^{20}$ are the same or different and, at each occurrence, independently hydrogen, alkyl, or substituted alkyl; q is 1 to 7; m is 2 to 1000; W is —O—, —S—, or —NH—; Y is —O—, —S—, or —NH—; and Z is —O—, —S—, or —NH—. In further embodiments, said polymer moieties are covalently bound to -L¹- with a structure having the following structural formula:

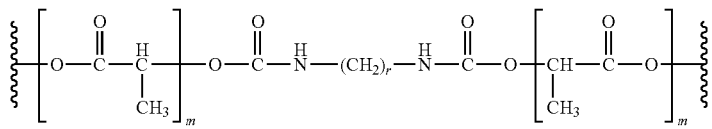

wherein r is 1 to 22, and m is 2 to 1000. In further embodiments, said polymer or polymer moiety has molecular weight over 1,000 and below 20,000, 20,000 and below 200,000; is over 200,000 and below 2,000,000; is over 2,000,000 and below, 20,000,000; or is over 20,000,000 and below 200,000,000.

In further embodiment, the invention relates to a method of making a material bioactive comprising: 1) providing: i) a material comprising: a) siloxane moieties, b) polymer groups, and c) linking groups; wherein said siloxane moieties are substituted with three or more of said polymer groups to form a siloxane-polyester conjugate; said linking groups join said conjugates through covalent bonds of said polymer groups, and wherein a portion of said linking groups comprise a first set of reactive groups; and ii) a bioactive substance comprising a second set of reactive groups; and 2) mixing said material and said bioactive substance under conditions such that a bioactive material formed by the reaction of said first reactive groups with said second reactive groups. In further embodiments, said first reactive groups are alkynyl groups. In further embodiments, said second reactive groups are —N₃ groups. In further embodiments, said first reactive groups are amine groups. In further embodiments, said second reactive groups are succinyl esters. In further embodiments, said bioactive substance comprises cationic or anionic moieties at physiological pH to form electrostatic interactions with target biomolecules. In further embodiments, said bioactive substance comprises hydrophilic moieties at physiological pH to form hydrogen-bonding interactions with target biomolecules. In further embodiments, said bioactive substance comprises a chemical moiety with acidic, basic, or neutral isoelectric points for the non-covalent adsorption of bioactive molecules with complementary isoelectric points (opposite net charges). In further embodiments, said chemical moiety is a peptide.

In some embodiments, the invention relates to a material comprising a polymer having the following structural formula:

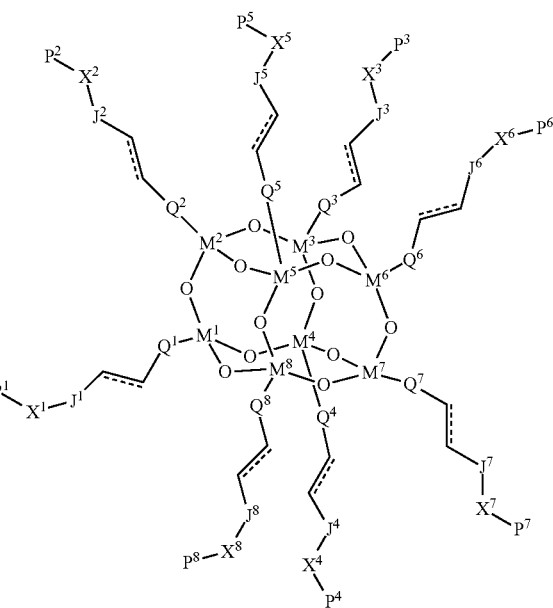

and salts thereof wherein, $P^1, P^2, P^3, P^4, P^5, P^6, P^7$, and $P^8$ are the same or different and, at each occurrence, independently hydrogen, a polymer moiety, a polymer linked to a bioactive substance or a polymer moiety covalently bound to a group having the following structural formula:

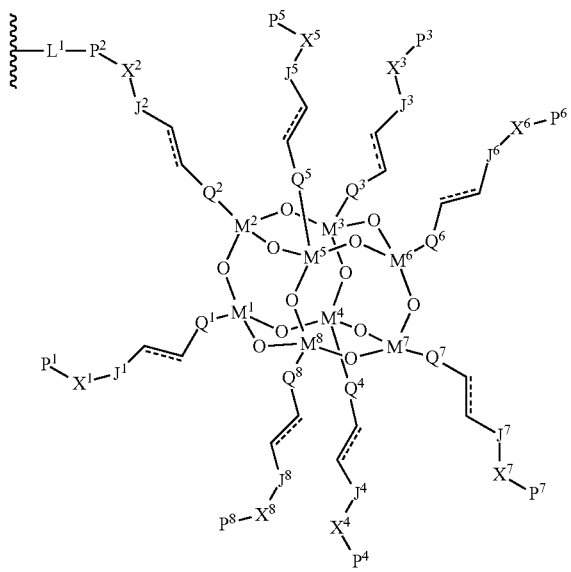

$L^1$ is a linking group, provided that at least three of said $P^1, P^2, P^3, P^4, P^5, P^6, P^7$, and $P^8$ have said polymer moieties covalently bound to said groups having said structural formula and provided that at least one $P^1, P^2, P^3, P^4, P^5, P^6, P^7$, and $P^8$ is a polymer moiety linked to a bioactive substance; $X^1, X^2, X^3, X^4, X^5, X^6, X^7$, and $X^8$ are the same or different and, at each occurrence, independently —O—, —S—, —NH—, —NR$^{21}$—, $J^1, J^2, J^3, J^4, J^5, J^6, J^7$, and $J^8$ are the same or different and, at each occurrence, independently joining groups; ▬▬ is a single or double bond; $Q^1, Q^2, Q^3, Q^4, Q^5, Q^6, Q^7, Q^8$ are the same or different and, at each occurrence, independently —O-M$^9$R$^1$R$^2$—, —O-M$^{10}$R$^3$R$^4$—, —O-M$^{11}$R$^5$R$^6$—, —O-M$^{12}$R$^7$R$^8$—, —O-M$^{13}$R$^9$R$^{10}$—, —O-M$^{14}$R$^{11}$R$^{12}$—, —O-M$^{15}$R$^{13}$R$^{14}$—, —O-M$^{16}$R$^{15}$R$^{16}$—, —O-M$^9$R$^1$R$^2$—, or absent forming a bond between adjacent atoms; $M^1, M^2, M^3, M^4, M^5, M^6, M^7, M^8, M^9, M^{10}, M^{11}, M^{12}, M^{13}, M^{14}, M^{15}$, and $M^{16}$ are the same or different and, at each occurrence, independently a metal or metalloid atom; $R^1, R^2, R^3, R^4, R^5, R^6, R^7, R^8, R^9, R^{10}, R^{11}, R^{12}, R^{13}, R^{14}, R^{15}$, and $R^{16}$ are the same or different and, at each occurrence, independently alkyl, —Oalkyl, or —Oaryl; and $R^{21}$ is alkyl. In further embodiments, said polymer moiety linked to said bioactive substance has the formula: $P^9$-$L^2$-Sub wherein, $P^9$ is a polymer moiety; $L^2$ is a linking group; and Sub is a bioactive substance. In further embodiments, said metal or metalloid atom is selected from the group consisting of Si, Ti, Zr, Li, Co, and Cr. In further embodiments, said joining groups are selected from the group consisting of —(CH$_2$)$_n$—, —(OCH$_2$CH$_2$)$_n$—, —(C═O)—, and —((C═O)O(CH$_2$)$_n$)— wherein n is 1 to 22. In further embodiments, $P^9$-$L^2$- has the following formula:

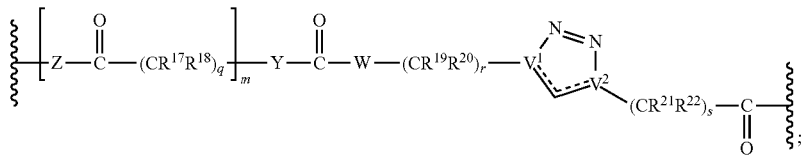

wherein $V^1$ is Nitrogen and $V^2$ is Carbon, or $V^1$ is Carbon and $V^2$ is Nitrogen; ▬▬ is a single or double bond s is 1 to 22, $R^{17}, R^{18}, R^{19}, R^{20}, R^{21}$, and $R^{22}$ are the same or different and, at each occurrence, independently hydrogen, alkyl, or substituted alkyl; q is 1 to 4, 5, or 7; m is 2 to 1000; W is —O—, —S—, or —NH—; Y is —O—, —S—, or —NH—; and Z is —O—, —S—, or —NH—. In further embodiments, said bioactive substance is a peptide. In further embodiments, $P^9$-$L^2$-Sub has the following structural formula:

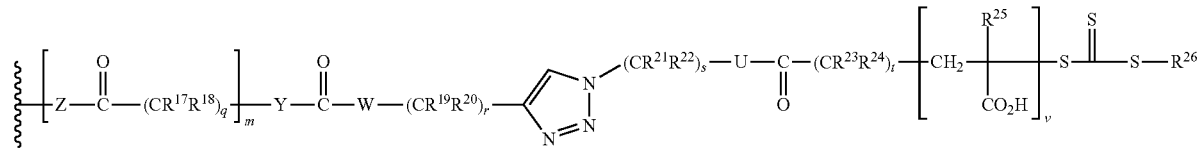

wherein, r is 1 to 22, s is 1 to 22, t is 1 to 22, $R^{17}$, $R^{18}$, $R^{19}$, $R^{20}$, $R^{21}$, $R^{22}$, $R^{23}$, $R^{24}$, $R^{25}$, and $R^{26}$ are the same or different and, at each occurrence, independently hydrogen, alkyl, or substituted alkyl; q is 1 to 4, 5, or 7; m is 2 to 1000; v is 1 to 1000; U is —O—, —S—, or —NH—; W is —O—, —S—, or —NH—; Y is —O—, —S—, or —NH—; and Z is —O—, —S—, or —NH—.

In some embodiments, the invention relates to composition comprising a polymer having the following structural formula:

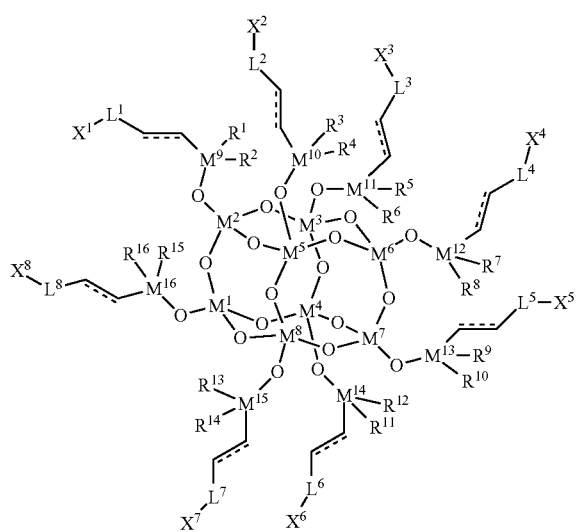

and salts thereof, wherein, $X^1$, $X^2$, $X^3$, $X^4$, $X^5$, $X^6$, $X^7$, and $X^8$ are the same or different and, at each occurrence, independently —OH, —SH, —NH$_2$, —CO$_2$H, a substrate, or a group having the following structural formula:

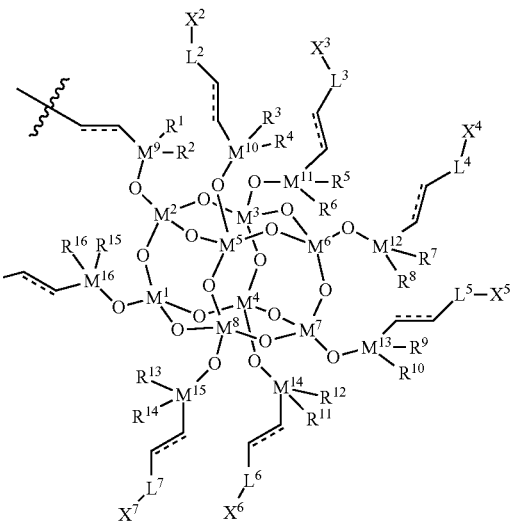

$L^1$, $L^2$, $L^3$, $L^4$, $L^5$, $L^6$, $L^7$, and $L^8$ are the same or different and, at each occurrence, independently linking groups; or ==== is a single or double bond; $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, and $M^{16}$ are the same or different and, at each occurrence, independently a metal or metalloid atom; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are the same or different and, at each occurrence, independently alkyl, —Oalkyl, or —Oaryl. In further embodiments, said metal or metalloid atom is selected from the group consisting of Si, Ti, Zr, Li, Co, and Cr. In still further embodiments, said linking groups are selected from the group consisting of —(CH$_2$)$_n$—, —(OCH$_2$CH$_2$)$_n$—, —(C=O)—, and —((C=O)O(CH$_2$)$_n$)— wherein n is 1 to 22. In certain embodiments, three or more $L^1$, $L^2$, $L^3$, $L^4$, $L^5$, $L^6$, $L^7$, and $L^8$ groups have the following structural formula:

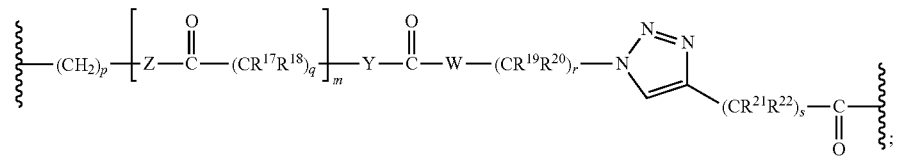

wherein p is 0 to 22, r is 1 to 22, s is 1 to 22, $R^{17}$, $R^{18}$, $R^{19}$, $R^{20}$, $R^{21}$, and $R^{22}$ are the same or different and, at each occurrence, independently hydrogen, alkyl, or substituted alkyl; q is 1 to 4; m is 10 to 100; W is —O—, —S—, or —NH—; Y is —O—, —S—, or —NH—; and Z is —O—, —S—, or —NH—. In further embodiments, said substrate is a peptide. In still further embodiments, said peptide is biocompatible or bioactive. In additional embodiments, at least three of -$L^1$-$X^1$, -$L^2$-$X^2$, -$L^3$-$X^3$, -$L^4$-$X^4$, -$L^5$-$X^5$, -$L^6$-$X^6$, -$L^7$-$X^7$, and -$L^8$-$X^8$ groups have the following structural formula:

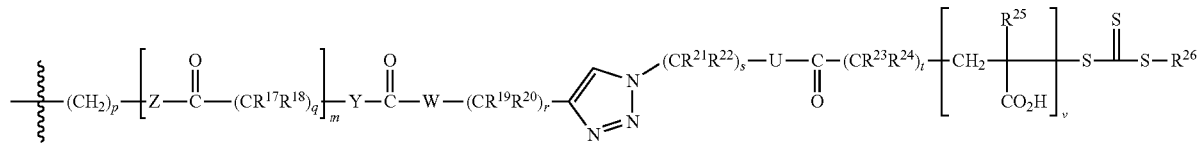

wherein p is 1 to 22, r is 1 to 22, s is 1 to 22, t is 1 to 22, $R^{17}$, $R^{18}$, $R^{19}$, $R^{20}$, $R^{21}$, $R^{22}$, $R^{23}$, $R^{24}$, $R^{25}$, and $R^{26}$ are the same or different and, at each occurrence, independently hydrogen, alkyl, or substituted alkyl; q is 1 to 4; m is 10 to 100; v is 1 to 100; U is —O—, —S—, or —NH—; W is —O—, —S—, or —NH—; Y is —O—, —S—, or —NH—; and Z is —O—, —S—, or —NH—. In certain embodiments, three or more $L^1$, $L^2$, $L^3$, $L^4$, $L^5$, $L^6$, $L^7$, and $L^8$ groups have the following structural formula:

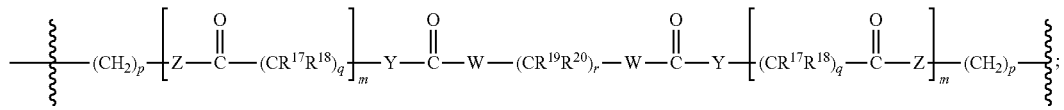

wherein p is 0 to 22, r is 1 to 22, $R^{17}$, $R^{18}$, $R^{19}$ and $R^{20}$ are the same or different and, at each occurrence, independently hydrogen, alkyl, or substituted alkyl; q is 1 to 4; m is 10 to 100; W is —O—, —S—, or —NH—; Y is —O—, —S—, or —NH—; and Z is —O—, —S—, or —NH—. In some embodiments, three or more $L^1$, $L^2$, $L^3$, $L^4$, $L^5$, $L^6$, $L^7$, and $L^8$ have the following structural formula:

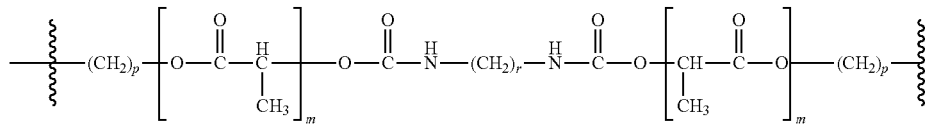

wherein p is 0 to 22, r is 1 to 22, and m is 10 to 100. In further embodiments, said polymer has molecular weight is over 100 and below 20,000; is over 20,000 and below 200,000; is over 200,000 and below 2,000,000; is over 2,000,000 and below, 20,000,000; or is over 20,000,000 and below 200,000,000.

In yet another embodiments, the invention relates to a material comprising: a) siloxane moieties substituted with polymer moieties b) a first set of linking groups, c) a second set of linking groups and d) a bioactive substance; wherein said first set of linking groups covalently join said siloxane moieties through said polymer moieties and said second set of linking groups join said bioactive substance to said polymer moieties through covalent or noncovalent bonds. In further embodiments, said bioactive substance is selected form the group consisting of a cell adhesive peptide, a nucleating ligand and growth factor. In further embodiments, said cell adhesive peptide comprises an RGD peptide sequence. In further embodiments, said nucleating ligand comprises a hydroxyapatite-binding peptide sequence. In further embodiments, said growth factor is an osteogenic growth factor. In further embodiments, said osteogenic growth factor comprises a bone morphogenetic protein 2 peptide sequence.

In some embodiments, the invention relates to a material comprising: a) siloxane moieties, b) linking groups, and c) a biocompatible or bioactive substance; said linking groups join said siloxane moieties and said biocompatible or bioactive biomolecule through covalent bonds. In other embodiments the material further comprises polymer groups, wherein said siloxane moieties are substituted with three or more of said polymer groups to form a siloxane-polymer conjugate; and said linking groups join said conjugates and said biocompatible or bioactive biomolecule through covalent bonds of said polymer groups. In further embodiments, said biocompatible or bioactive substance is selected form the group consisting of a cell adhesive peptide, a nucleating ligand and growth factor. In further embodiments, said cell adhesive peptide comprises an RGD peptide sequence. In further embodiments, said nucleating ligand comprises a hydroxyapatite-binding peptide sequence. In further embodiments, said growth factor is an osteogenic growth factor. In further embodiments, said osteogenic growth factor comprises a bone morphogenetic protein 2 peptide sequence.

In some embodiments, the invention relates to a degradable shape memory polymer composition comprising: a) POSS unit functionalized with a polylactone, and b) urethane crosslinks. In further embodiment, said polylactone has a stereocenter. In further embodiments, said polylactone is polylactide.

In other embodiments, the invention relates to a compound having the following formula:

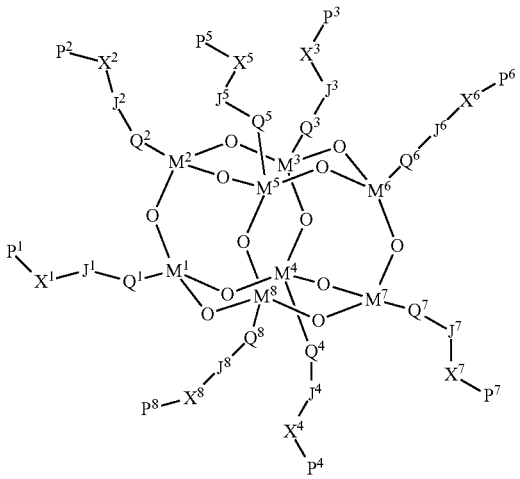

wherein, $Q^1$, $Q^2$, $Q^3$, $Q^4$, $Q^5$, $Q^6$, $Q^7$, $Q^8$ are the same or different and, at each occurrence, independently —O-$M^9R^1R^2$—, —O-$M^{10}R^3R^4$—, —O-$M^{11}R^5R^6$—, —O-$M^{12}R^7R^8$—, —O-$M^{13}R^9R^{10}$—, —O-$M^{14}R^{11}R^{12}$—, —O-$M^{15}R^{13}R^{14}$—, —O-$M^{16}R^{15}R^{16}$—, —O-$M^9R^1R^2$—, or absent forming a bond between adjacent atoms; $J^1$, $J^2$, $J^3$, $J^4$, $J^5$, $J^6$, $J^7$, and $J^8$ are the same or different and, at each occurrence, independently groups;

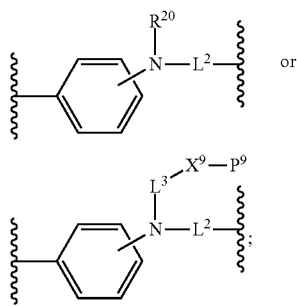

$L^2$, and $L^3$ are linking groups comprising an alkyl or substituted alkyl; $P^1$, $P^2$, $P^3$, $P^4$, $P^5$, $P^6$, $P^7$, $P^8$, and $P^9$ are the same or different and, at each occurrence, independently a hydrogen or a polymer moiety comprising a reactive group; $X^1$, $X^2$, $X^3$, $X^4$, $X^5$, $X^6$, $X^7$, $X^8$ and $X^9$ are the same or different and, at each occurrence, independently —O—, —S—, —NH—, or —$NR^{19}$—; $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, and $M^{16}$ are the same or different and, at each occurrence, independently a metal or metalloid atom; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are the same or different and, at each occurrence, independently alkyl, substituted alkyl, aryl, substituted aryl, —Oalkyl, substituted —Oalkyl, —Oaryl, or substituted —Oaryl; $R^{19}$ is alkyl; and $R^{20}$ is hydrogen or alkyl.

In some embodiments, the invention relates to a material comprising a polymer having the following structural formula:

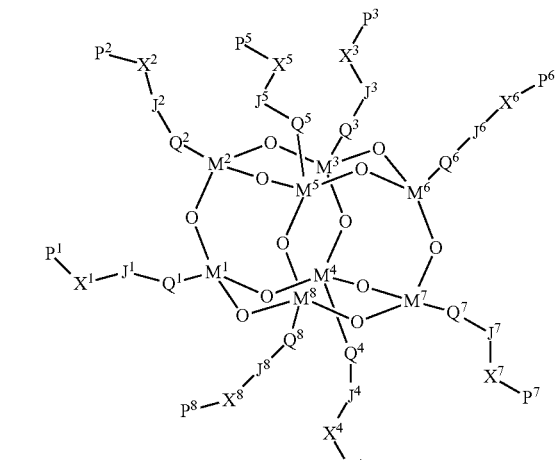

and salts thereof wherein, $Q^1$, $Q^2$, $Q^3$, $Q^4$, $Q^5$, $Q^6$, $Q^7$, $Q^8$ are the same or different and, at each occurrence, independently —O-$M^9R^1R^2$—, —O-$M^{10}R^3R^4$—, —O-$M^{11}R^5R^6$—, —O-$M^{12}R^7R^8$—, —O-$M^{13}R^9R^{10}$—, —O-$M^{14}R^{11}R^{12}$—, —O-$M^{15}R^{13}R^{14}$—, —O-$M^{16}R^{15}R^{16}$—, —O-$M^9R^1R^2$—, or absent forming a bond between adjacent atoms; $P^1$, $P^2$, $P^3$, $P^4$, $P^5$, $P^6$, $P^7$, $P^8$ and $P^9$ are the same or different and, at each occurrence, independently hydrogen, a polymer moiety, a polymer linked to a bioactive substance or a polymer moiety covalently bound to a group having the following structural formula:

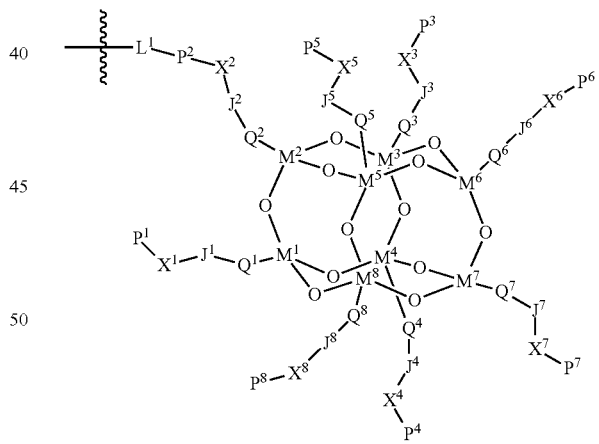

$L^1$ is a linking group, provided that at least three of said $P^1$, $P^2$, $P^3$, $P^4$, $P^5$, $P^6$, $P^7$, and $P^8$ have said polymer moieties covalently bound to said groups having said structural formula and provided that at least one $P^1$, $P^2$, $P^3$, $P^4$, $P^5$, $P^6$, $P^7$, and $P^8$ is a polymer moiety linked to a bioactive substance; $X^1$, $X^2$, $X^3$, $X^4$, $X^5$, $X^6$, $X^7$, $X^8$ and $X^9$ are the same or different and, at each occurrence, independently —O—, —S—, —NH—, or —$NR^{21}$—, $J^1$, $J^2$, $J^3$, $J^4$, $J^5$, $J^6$, $J^7$, and $J^8$ are the same or different and, at each occurrence, independently joining groups or joining group having the following structure;

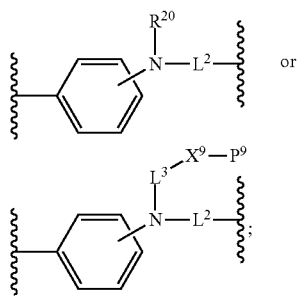

$L^2$, and $L^3$ are linking groups; $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, and $M^{16}$ are the same or different and, at each occurrence, independently a metal or metalloid atom; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are the same or different and, at each occurrence, independently alkyl, —Oalkyl, or —Oaryl; and $R^{21}$ is alkyl. In further embodiments, more than half of the metal and metalloid atoms are Si.

In yet other embodiments, the invention relates to a compound of the formula:

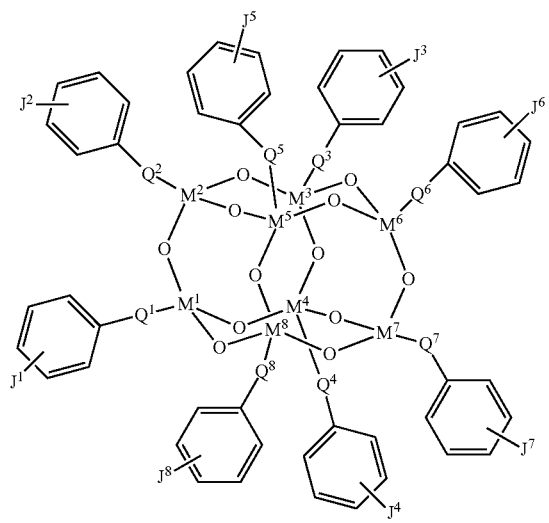

wherein, $Q^1$, $Q^2$, $Q^3$, $Q^4$, $Q^5$, $Q^6$, $Q^7$, $Q^8$ are the same or different and, at each occurrence, independently —O-$M^9R^1R^2$—, —O-$M^{10}R^3R^4$—, —O-$M^{11}R^5R^6$—, —O-$M^{12}R^7R^8$—, —O-$M^{13}R^9R^{10}$—, —O-$M^{14}R^{11}R^{12}$—, —O-$M^{15}R^{13}R^{14}$—, —O-$M^{16}R^{15}R^{16}$—, —O-$M^9R^1R^2$—, or absent forming a bond between adjacent atoms; $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, and $M^{16}$ are the same or different and, at each occurrence, independently a metal or metalloid atom; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are the same or different and, at each occurrence, independently alkyl, substituted alkyl, aryl, substituted aryl, —Oalkyl, substituted —Oalkyl, —Oaryl, or substituted —Oaryl; $J^1$, $J^2$, $J^3$, $J^4$, $J^5$, $J^6$, $J^7$, and $J^8$ are the same or different and, at each occurrence, independently groups;

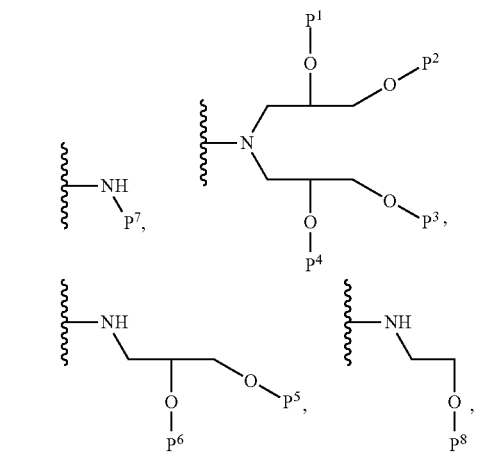

or —$X^1$-$L^1$-$P^9$; $X^1$ is —O—, —S—, —NH—, or —$NR^{21}$; $L^1$ is a linking group; $R^{21}$ is hydrogen or alkyl; and $P^1$, $P^2$, $P^3$, $P^4$, $P^5$, $P^6$, $P^7$, $P^8$ and $P^9$ are the same or different and, at each occurrence, independently hydrogen or a polymer moiety with a reactive group. In further embodiments, three or more of said polymer moieties have the following structural formula:

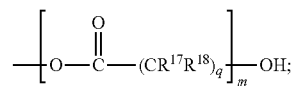

wherein, $R^{17}$ and $R^{18}$ are the same or different and, at each occurrence, independently hydrogen, alkyl, or substituted alkyl; q is 1 to 4, 5, or 7; and m is 2 to 1000. In further embodiments, three or more of $P^1$, $P^2$, $P^3$, $P^4$, $P^5$, $P^6$, $P^7$, and $P^8$ have the following structural formula:

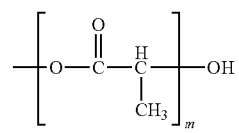

wherein m is 2 to 1000.

In some embodiments, the invention relates to compounds, polymers, and materials disclosed herein that have three or more of said polymer moieties having a terminal alkenyl group for crosslinking by radical polymerization such as those with the following structural formula:

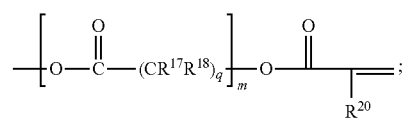

wherein, $R^{17}$ and $R^{18}$ are the same or different and, at each occurrence, independently hydrogen, alkyl, or substituted alkyl; $R^{20}$ is hydrogen or alkyl; q is 1 to 4, 5, or 7; and m is 2 to 1000.

In some embodiments, the invention relates to materials made by crosslinking the compounds disclosed herein.

In other embodiments, the invention relates to the use of compositions and materials disclosed herein for medical devices, such as self-expanding stents, intravascular thrombectomy devices, sutures, replacements for ocular tissue, scaffolds for tissue regeneration, orthopedic implants for the fixation of bone fragments and fractures, tubular vascular implants for the prophlaxis of restenosis, actuators and catheters to remove matter from a vessel, biostable catheter distal tips and actuators for intravascular use and other minimally invasive operations, to fortify an intervertebral disc having an annulus fibrosis with an inner ball, as a self-expanding frame to be fastened to the inner wall of the annulus, self-tightening sutures to close a wound of body scission.

In some embodiments, the invention relates to the use of compositions and materials disclosed herein for to eyeglass frames, sporting goods, toys, automobile parts, space structures, fabrics, rewritable digital storage media.

In some embodiments, the invention relates to the use of compositions and materials disclosed herein for the reconstruction of functional tissues by the degration or release of bioactive substances on demand, inducing forces on seeded cells, or inducing proliferation and differentiation of cells.

In some embodiments, the invention relates to the use of compositions and materials disclosed herein for the prevention or treatment of diseases and disorders associated with the gastrointestinal tract. In further embodiments, a device is configured to reduce the volume of the stomach, esophagus, or intestine without interfering with the flow of food through the gastrointestinal tract. In further embodiments, a device comprising materials and compositions disclosed herein is used to facilitate weightloss. In further embodiments, a device comprising materials and compositions disclosed herein is used to deliver a drug.

In some embodiments, the invention relates to the compositions and materials disclosed herein in a pharmaceutical composition.

In some embodiments, the invention relates to a material comprising: siloxane moieties, polymer groups, linking groups, and at least one inorganic mineral wherein said siloxane moieties are substituted with three or more of said polymer groups to form a siloxane-polymer conjugate; said linking groups join said conjugates through covalent bonds of said polymer groups, and said inorganic mineral intercalated within said siloxane, said polymer and said linking groups to form a siloxane-polymer-inorganic mineral conjugate. The inorganic mineral is interspersed within the framework of the conjugate material in a non-covalently bound arrangement. In further embodiments, said siloxane moieties are octakis(hydridodimethylsiloxy)octasesquioxanes. In still further embodiments, said polymer groups are polyester groups. In additional embodiments, said material has one-way or two-way shape memory. In additional embodiments, the inorganic mineral is selected from the group consisting of calcium carbonate, calcium phosphate, calcium hydroxyapatite, carbonated hydroxyapatite and beta-tricalcium phosphate. In some embodiments, said inorganic mineral comprises between 0.1% and 90% by weight of said material.

In some embodiments, the invention relates to a method of making a material suitable for biomedical use comprising: providing at least one inorganic mineral and a first compound, said first compound comprising siloxane moieties, polymer groups and linking groups wherein said siloxane moieties are substituted with three or more of said polymer groups to form a siloxane-polyester conjugate; said linking groups join said conjugates through covalent bonds of said polymer groups and wherein a portion of said linking groups comprise a first set of reactive groups; mixing said inorganic mineral with said compound under conditions such that said inorganic mineral intercalates. In further embodiments, said siloxane moieties are octakis(hydridodimethylsiloxy)octasesquioxanes. In still further embodiments, said polymer groups are polyester groups. In additional embodiments, said first reactive groups are alkynyl groups. In some embodiments, said first reactive groups are amine groups. In further embodiments, said material has one-way or two-way shape memory. In still further embodiments, said biomedical use is bone substitution.

In some embodiments, the invention relates to a method of making a material suitable for biomedical use comprising: providing siloxane moieties, polymer groups, and linking groups and substituting said siloxane moieties with three or more of said polymer groups to form a siloxane-polyester conjugate; said linking groups joining said conjugates through covalent bonds of said polymer groups, and wherein a portion of said linking groups comprise a first set of reactive groups. In further embodiments, said siloxane moieties are octakis(hydridodimethylsiloxy)octasesquioxanes. In still further embodiments, said first reactive groups are alkynyl groups. In additional embodiments, said first reactive groups are amine groups. In additional embodiments, said material has one-way or two-way shape memory. In some embodiments, said material suitable for biomedical use is selected from the group consisting of stitches, stents, sutures, orthopedic supports and surgical supports. In further embodiments, said polymer groups are polyester groups. In additional embodiments, said material has a $T_g$ between 17° C. and 100° C. In some embodiments, said material has a $T_g$ between 37° C. and 50° C. In further embodiments, said siloxane moieties are selected from the group consisting of silsesquioxanes and metallasiloxanes. In some embodiments, said siloxane moieties are caged structures. In further embodiments, said siloxane moieties are octakis(hydridodimethylsiloxy)octasesquioxanes. In still further embodiments, said polyester groups are polylactones. In additional embodiments, said linking groups comprise alkyl, aryl, or polyethylene groups. In some embodiments, said linking groups comprise urethane groups. In further embodiments, said material is porous. In still further embodiments, said porosity is between 0.1% and 90%. It is not intended that the present invention be limited to the method of fabrication by which said porosity is incorporated into the present invention. Preferred methods of fabrication include but are in no way limited to salt-leaching, porogen leaching, thermally induced phase separation, and solid freeform fabrication techniques.

In some embodiments, the invention relates to a method of supplementing or repairing a bone in a subject comprising: providing a material comprising: siloxane moieties, polymer groups, linking groups, and at least one inorganic mineral wherein said siloxane moieties are substituted with three or more of said polymer groups to form a siloxane-polymer conjugate, said linking groups join said conjugates through covalent bonds of said polymer groups, said inorganic mineral intercalated within said siloxane, and said polymer and said linking groups to form a siloxane-polymer-inorganic mineral conjugate; a subject suspected of or exhibiting symptoms associated with a bone disorder or dysfunction and administering said material to said subject under conditions such that said bone disorder or dysfunction is reduced. In further embodiments, said siloxane moieties are octakis(hydridodimethylsiloxy)octasesquioxanes. In still further embodiments, said polymer groups are polyester groups. In additional embodiments, said polyester groups are polylactones. In some embodiments, said linking groups comprise alkyl, aryl, or polyethylene groups. In further embodiments, said linking groups comprises urethane groups. In still further embodiments, said mode of administration is surgical implantation. In additional embodiments, the bone exhibiting said bone disorder or dysfunction is selected frQm the group consisting of cracnial bones, mandible, ulna, humerus, radius, vertebrae, carpals, metacarpals, phalanges, ilium, ischium, pubis, femur, hip joint, patella, tibia, fibula, tarsals and metatarsals. In some embodiments, said bone disorder or dysfunction is selected from the group consisting of bone fracture, bone cyst, bone spur, bone tumor, craniosynostosis, fibrodysplasia ossificans progressiva, fibrous dysplasia, giant cell tumor of bone, hypophosphatasia, Klippel-Feil syndrome, metabolic bone disease, osteitis deformans, osteitis fibrosa cystica, osteitis pubis, condensing osteitis, osteitis condensans ilii, osteochondritis dissecans, osteochondroma, osteogenesis imperfecta, osteomalacia, osteomyelitis, osteopenia, osteopetrosis, osteoporosis, osteosarcoma, porotic hyperostosis, primary hyperparathyroidism and renal osteodystrophy. In further embodiments, said subject is a mammal.

In some embodiments, the invention relates to a method, comprising hydrosilyating octakis(dimethylsiloxy)octasilsesquioxane (POSS) by allyl alcohol under conditions such that an octahedral hydroxylated POSS core is formed; and grafting a biodegradable polylactide to said core to create a macromer. In further embodiments, said conditions of step a) comprise a catalyst. In still further embodiments, said catalyst is platinum divinyltetramethyldisiloxane. In additional embodiments, said grafting is achieved by ring opening polymerization of cyclic racemic lactide. In some embodiments, said polymerization is catalyzed by stannous octoate.

BRIEF DESCRIPTION OF THE FIGURES

FIG. 7I summarizes some of the properties of the present invention as described in FIGS. 7G and 7H. The dynamical mechanical properties were measured on a DMA Q800 (TA Instrument), which has a force resolution of 0.00001N and a displacement resolution of 1.0 nm. With temperature sweeping from 25.0° C. to 110° C. at a rate of 2.0° C./min, the samples were subjected to an oscillated deformation with constant strain of 0.02% at 1 Hz. The storage modulus, loss modulus and loss angel (Tan delta) were recorded with temperature.

FIG. 8H illustrates examples of the molecules generalized in FIG. 8G.

DETAILED DESCRIPTION OF THE INVENTION

The invention relates to materials comprising siloxanes, preferably the materials have thermal-responsive properties. In some embodiments, the invention relates to silsesquioxane groups functionalized with polymers. In another embodiment, silsequioxane-polymer conjugates comprise polylactone segments. The silsequioxane-polymer conjugates may be crosslinked together to form a material, and these materials may be functionalized with bioactive compounds so that the materials have desirable biocompatibility or bioactivity when used in medical devices. In further embodiments, the invention relates to composite materials that contain a polymer matrix and aggregates, and in some embodiments, methods of making, and methods of using these materials. Preferably, the aggregates are calcium phosphate aggregates. Preferably, the material is resistant to fracture. In further embodiments, the materials are used in surgical procedures of bone replacement. In further embodiments, the materials contain polyhedral silsesquioxanes and/or biodegradable segments.

Figure 12:
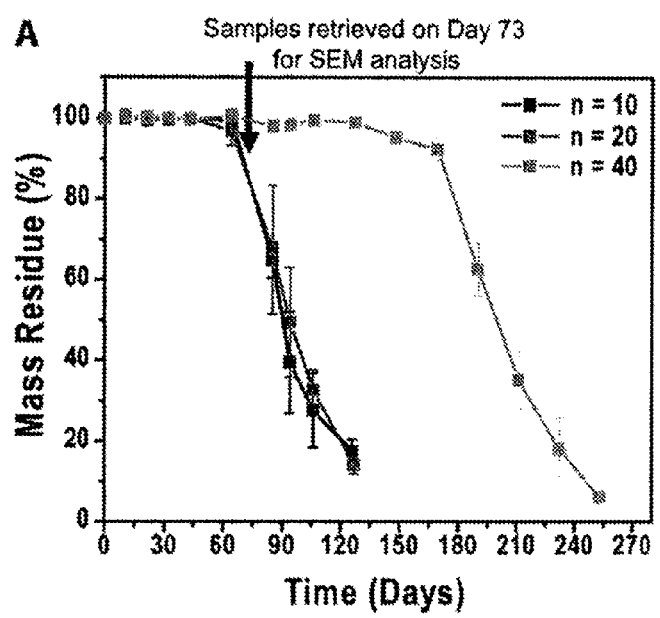
FIG. 12 shows in vitro degradation of a urethane-crosslinked macromer of the present invention, POSS-$(PLA_n)_8$, as a function of PLA chain length, wherein n=10, 20, 40. Panel A shows the percentage of mass reduction of crosslinked macromer 2 in PBS (pH 7.4) as a function of time. Panels B-G show SEM micrographs of the smooth surfaces prior to hydrolytic degradation (B: n=10; C: n=20; D: n=40) and the morphology of the materials after 73 days in PBS (E: n=10; F: n=20; G: n=40). Scale bars: 50 µm. A sample size of 3 was applied (N=3).
Figure 12:
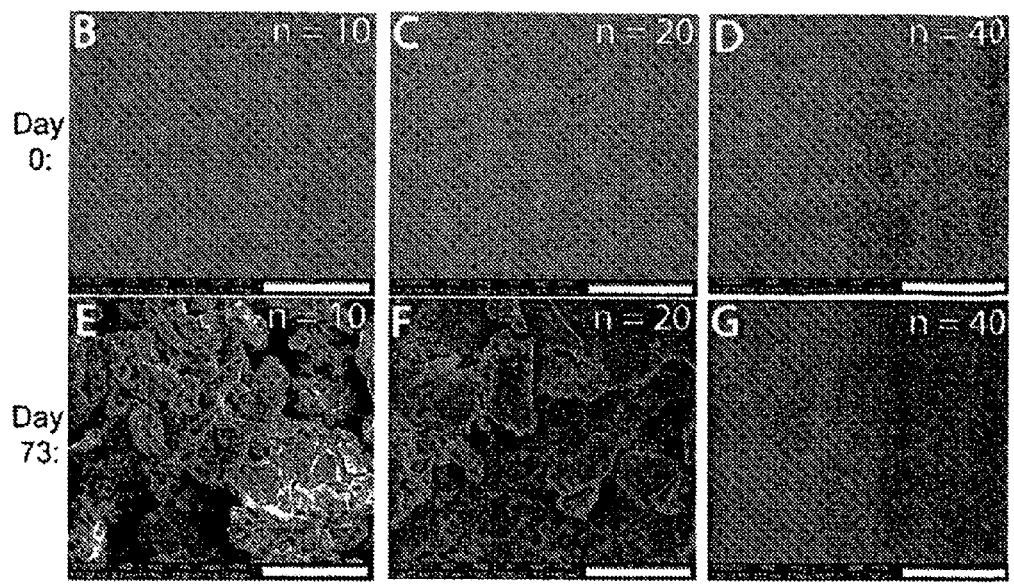

Embodiments of the invention concern a class of POSS-strengthened biodegradable shape memory polyester-urethanes that exhibit desired characteristics. A system is designed to provide a chemically crosslinked thermoset, which exhibits a transition of storage modulus around its glass transition temperature. The materials are prepared by the chemical crosslinking, i.e., preferably by the formation of urethane linkages with hexamethylene diisocyanate of multifunctional hybrid polyester, which are synthesized by ring opening polymerization of cyclic monomers such as, but not limited to, lactide, glycolide and caprolactone. The polyester-urethane solution can be cast into molds and crosslinked to form films or bulk materials with desired shapes (FIG. 12). The permanent shape can be easily deformed when heated above the transformation temperature; the deformed shape can be fixed at room temperature and preserved for a sufficient time, e.g., greater than 1 month. When heated again the deformed shape can recover to its original shape rapidly, e.g., within 1 second (FIG. 12). Responsive shape recovery times of this material is 300 times less than those disclosed in Lendlein et al., *Journal of Polymer Science Part A-Polymer Chemistry* 43, 1369 (2005), incorporated herein by reference. A number of methods can be used to trigger the transition of the polymer from its temporary shape to its permanent shape. For example, a resistive heater of radio frequency (RF) heater can be used. Alternatively or in addition, the polymer can be formulated to incorporate magnetic particles that are susceptible to heating by magnetic effects. The incorporation of the POSS cores reduces the crystallinity of the polyesters and results in the formation of amorphous polyester-urethane network with adjustable glass transition temperature and a transparent appearance.

Embodiments of the invention have the advantages to known materials in that they have 1) lighter weights and larger recoverable deformation ranges (up to several hundred percent strain), 2) more tunable mechanical properties and glass transition temperatures ($T_g$'s) that are suitable for biological applications, and 3) better chemical functionalizability to improve their biodegradability and biocompatibility or bioactivity. To the applicant's knowledge, tunable biodegradability with substantial shape memory effect has not been demonstrated with any single shape-memory material previously.

The present invention may be developed in a biodegradable material that may be further engineered with cortical-bone like mechanical properties, physiologically relevant glass transition/triggering temperatures, tunable biodegradation rates matching with normal fracture healing and spinal fusing rates, and surface functionality facilitating the materials' in vivo integration with host tissue. Therefore, these biodegradable shape memory polymers may be used, for example, as deployable synthetic bone substitutes/grafts for a wide range of orthopedic applications, including craniofacial reconstruction, the repair of critical-sized bony defects due to tumor resection, the repair of skeletal trauma, the surgical fixation of hard-to-heal fractures such as osteoporotic fractures, diabetic fractures and periarticular fractures (such as tibia plateau and distal radius fractures) and minimally invasive vertebroplasty procedures. They may further be utilized as self-expanding frames for spinal fusion applications. Synthetic bone substitutes currently comprise >50% of the multi-billion dollar spine fusion product market. It is estimated that 50 million Americans suffer lower back pain, with an increasing number of these individuals seeking surgical intervention to relieve the symptom. Because of the prevalence of cancer, osteoporosis, diabetes, degenerative disc diseases in the aging society, synthetic bone substitutes/grafts market, particularly the ones without any animal tissues, is not only an established one, but also a steadily growing one.

The biodegradable shape memory polymers of the present invention can be used as resorbable anchors, plates and screws for orthopedic applications, some of which are mentioned above. They may also be used as dental fillers. Other biomedical applications of the shaoe memory polymers (SMP) include cardiovascular stents, actuators and catheters, self-tightening sutures, and resorbable drug-delivery scaffolds where temporary mechanical strength is desired. For instance, a drug-releasing and bioresorbable SMP stent will have major advantages over metallic stents (shape memory alloys, SMA) that are prevalently used today due to their ability to deliver drugs in a sustained manner, better mechanical compatibility with blood vessels, and the ability to biodegrade in programmable timeframes. SMPs can also be engineered with non-biodegradable chemical content. Non-biodegradable shape memory polymers requiring shape memory efficiency superior to those of the leading commercial products (e.g. Veriflex® from Cornerstone Research Group) can be developed using the present invention. Traditional applications for these materials include reusable molds, transforming toys, shape-changing furniture, deployment mechanisms, custom containers, shipping/packaging, actuators, thermal sensors, smart textile products in outerwear, sportswear and self-deployable units in spacecrafts, etc. Biodegradable embodiments of the present invention can further be applied to the manufacturing of environmentally friendly, or "green", toys.

Figure 7A:
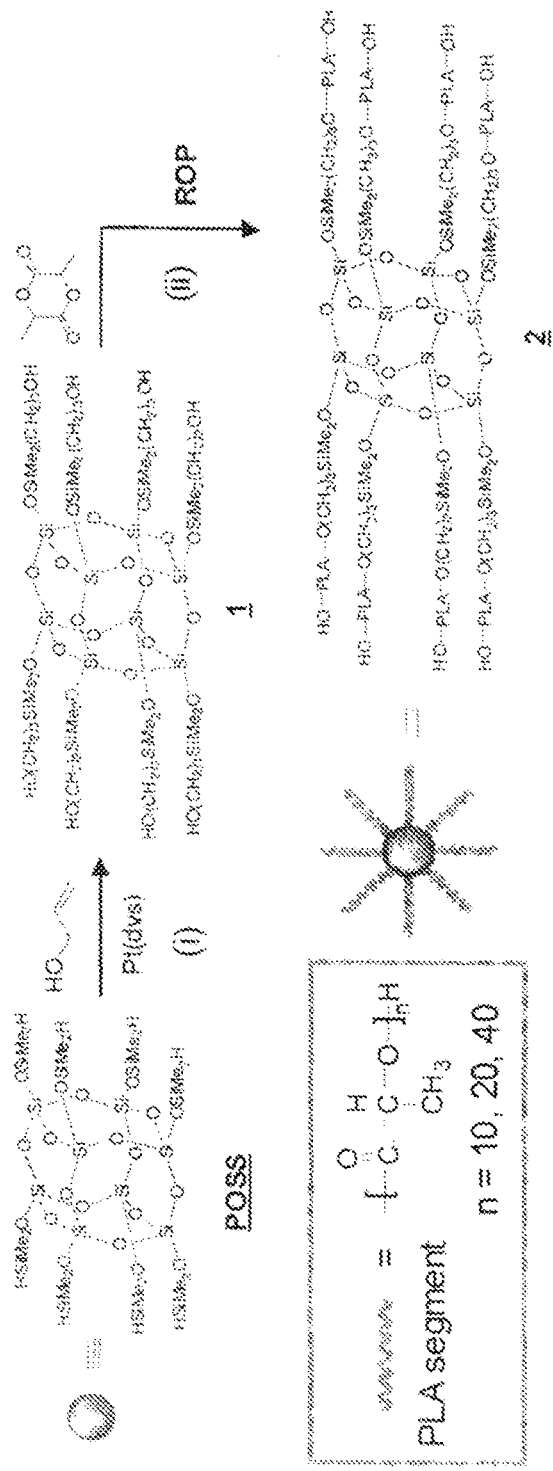
FIG. 7A shows a preferred method of making embodiments. It illustrates the synthesis of macromer 2 wherein (i) is carried out using 15 eq. allyl alcohol, $6\times10^{-4}$ eq. Pt(dvs), 20° C., 1 h, followed by 90° C., 1.5 h, $N_2$; and (ii) is carried out as follows: 40, 80 or 160 eq. rac-lactide, 200 ppm stannous octoate, 115° C., $N_2$, 20 h.

Altehel et al., *Angew. Chem. Int. Ed.* 44, 1188-1192 (2005), incorporated herein by reference, discloses a biodegradable material of copoly-ester-urethane networks that exhibits shape memory properties. The applicants have developed an improved material with a $T_g$ close to physiological temperature (thus with minimal potential cell/tissue damages during thermal triggering), attractive physical appearance (e.g.

transparent), biodegradability and tunable mechanical strength (e.g. storage modulus in the same range of cortical bone). Embodiments of the invention are illustrated in FIG. 7A. Polyhedral silsesquioxane (POSS) nanoparticles are designed as a structural anchor to grow, and mechanically strengthen, star-shape biodegradable polyesters.

Figures 7B, 7C:
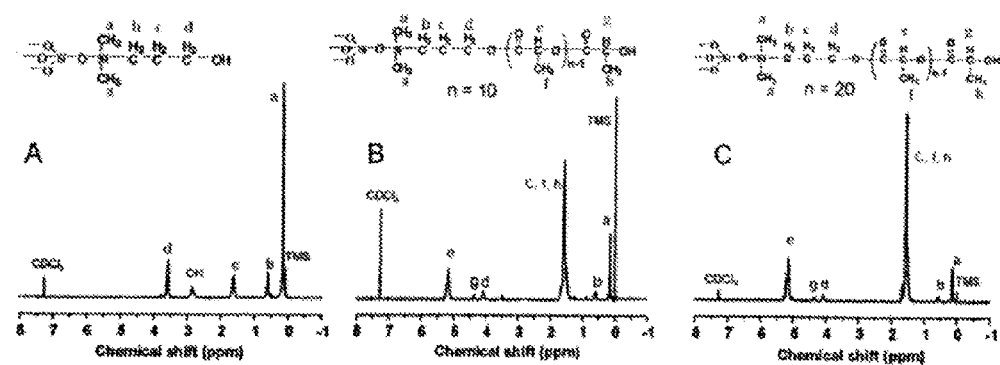
FIG. 7B shows the $^1H$ NMR spectra for a monomer (A) and n=10 (B) and n=20 (C) macromers of the invention.
FIG. 7C shows the estimated and determined molecular mass for the n=10 and n=20 macromers disclosed in FIG. 7B as well as an n=40 macromer. Table Legend: "Theoretical"=theoretical molecular mass of the disclosed macromers; "GPC"=molecular mass of the disclosed macromers as determined by gel permeation chromatography; "NMR"=calculated molecular mass of the disclosed macromers as determined by NMR peak area integration; "PDI"=polymer dispersion index of the disclosed macromers.
Figure 7D:
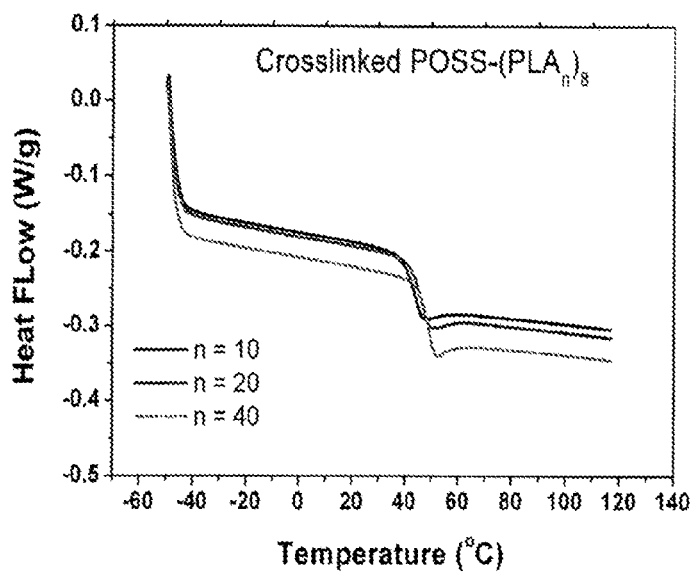
FIG. 7D shows differential scanning calorimetry (DSC) traces of crosslinked POSS-$(PLA_n)_8$ urethane with a heating rate of 10° C./min.
Figure 7E:
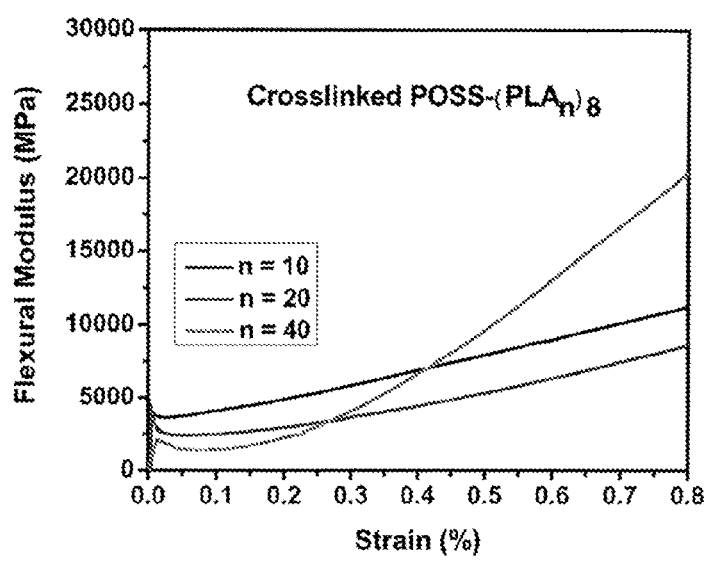
FIG. 7E shows data of flexural moduli of urethane-crosslinked POSS-$(PLA_n)_8$ as a function of PLA chain length in preferred embodiments.
Figure 7F:
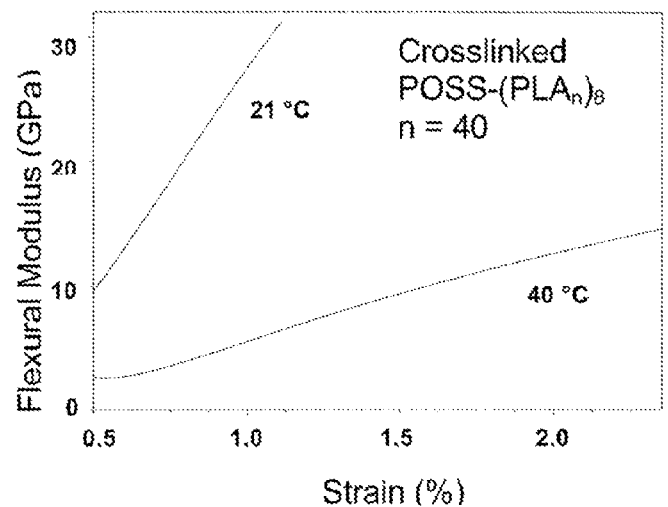
FIG. 7F shows data of flexural moduli as a function of temperature in preferred embodiments.
Figure 7G:
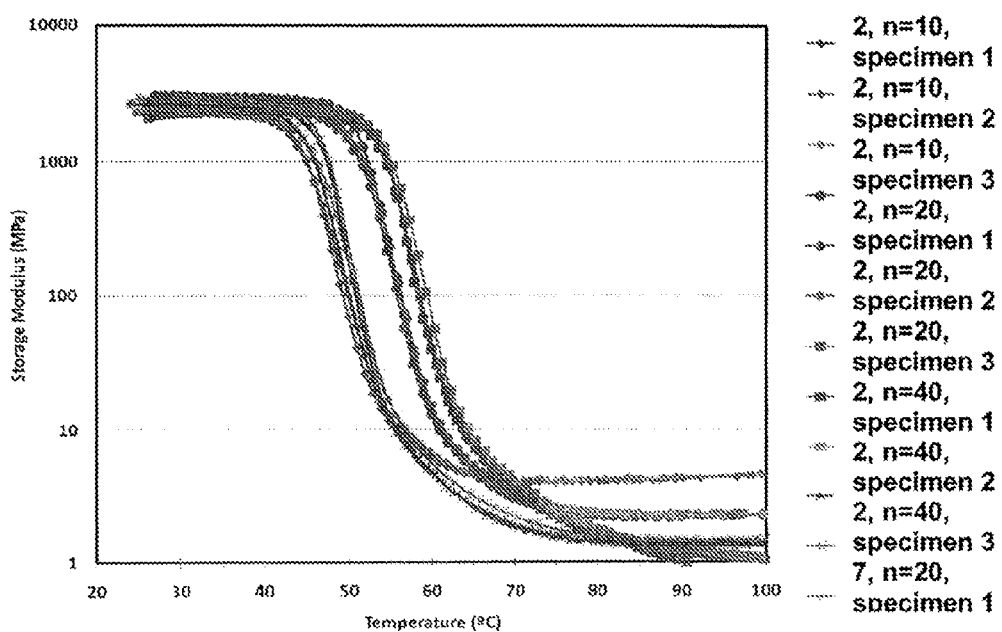
FIGS. 7G and 7H show dynamic mechanical properties (storage moduli and tan delta) of the urethane-crosslinked macromer 2 (FIG. 7A) and 7 (FIG. 8C) as a function of PLA chain length and temperature.
Figure 7H:
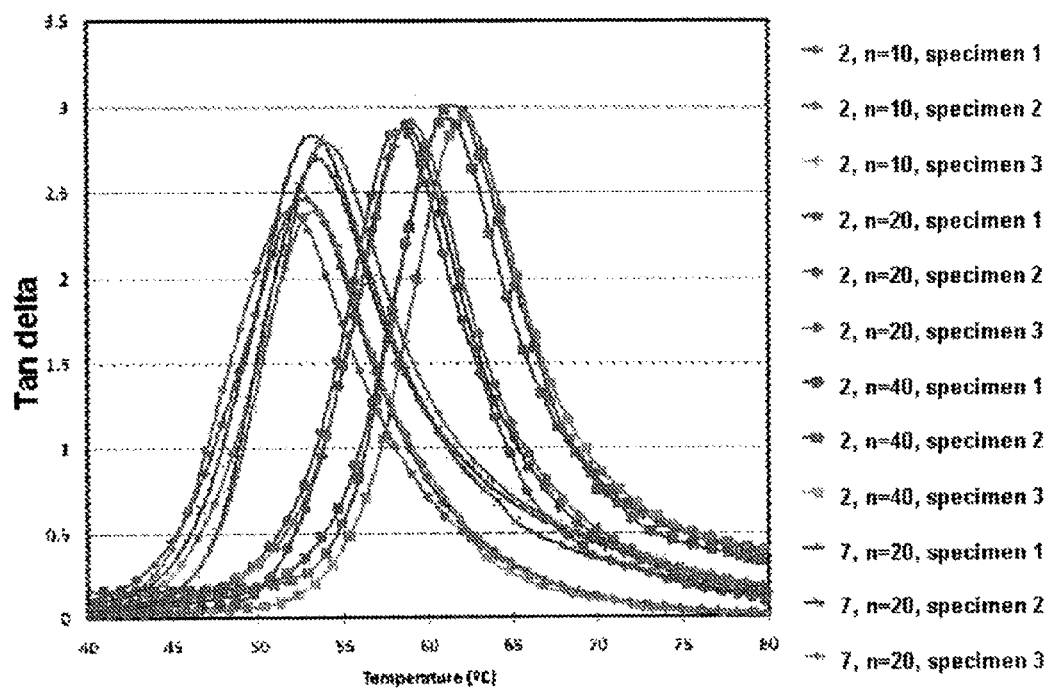
Figure 7J:
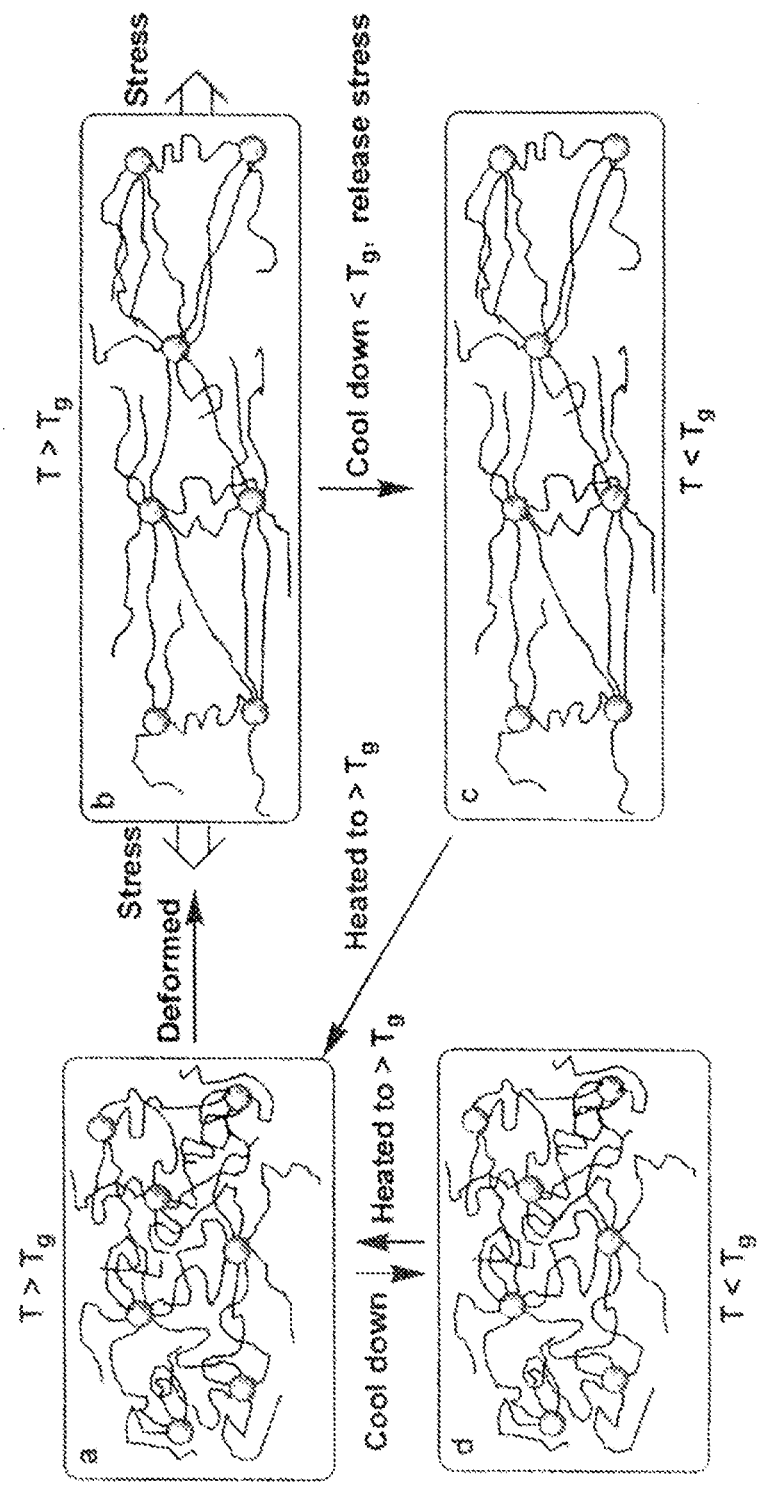
FIG. 7J illustrates a proposed shape memory mechanism even though the applicant does not intend that the invention be limited to any particular mechanism.

Known SMPs require low temperature for fixing their "temporary" shapes and/or high temperature for triggering the shape recovery. In addition, their performances are often limited by slow recovery rates and weak recovery stress. POSS-poly(ester-urethane) SMP can be easily deformed from a coiled permanent shape ($T_g$ ~44° C.) into a flat temporary shape when heated to 50° C. This temporary shape can be preserved at room temperature with almost no shape distortion over many months. When a 50° C. temperature was applied, however, the material recovered to its original coil shape within 1 sec. POSS-poly(ester-urethane) SMP's are transparent, owing to their amorphous polymer chain structure arrangements. Although the applicant does not intend embodiments of the invention to be limited to any particular shape, it is believed that the observed efficient shape memory behavior is due to the unique combination of the elasticity of the polylactide (PLA) chains and the rigidity of the POSS nanoparticle cores (FIG. 7J).

To be utilized as or incorporated into functional biomedical devices such as tissue engineering grafts, it is preferred that SMPs exhibit biocompatibility or bioactivity, biodegradability, efficient shape memory behavior near physiological temperature, appropriate mechanical properties, and bioactivities specific to their intended applications. To the best of our knowledge, no SMP reported to date can fulfill all these requirements. Embodiments of the invention disclosed herein are biodegradable, have excellent shape memory behavior, and exhibit robust mechanical strength. In order to enhancing biocompatibility and bioactivity one can make chemical modifications without perturbing mechanical and shape memory properties. Specifically, one can functionalize the POSS-poly(ester-urethane) with cell adhesive peptides, mineral-nucleating ligand and growth factor-retention domain to improve its biological performance as synthetic bone graft materials.

It is preferable to have favorable cell-material interactions at the tissue-graft interface when integrating a synthetic graft with its tissue environment. One can attach an RGD epitope on the SMP to improve the recruitment osteoblast precursor cells to the synthetic bone graft.

It is preferred to design polymer bone grafts with the ability of the graft to template the nucleation and growth of hydroxyapatite (HA), the major mineral component of bone, in situ. HA-binding peptide can act as a template for the growth of crystalline HA in vitro. It is believed that attachment of HA-binding peptide can enhance the SMP bone graft's bonding affinity to the surrounding bony tissue and its ability to template HA deposition in vivo as described in Bertozzi et al. WO Patent Application No. PCT/US 2005/43214, hereby incorporated by reference.

Fracture repair of bony defects can be promoted by the exogenous supply of osteogenic growth factor human recombinant bone morphogenetic protein 2 (rhBMP-2). We propose to locally retain the alkaline rhBMP-2 (isoelectric point: 9.3) on the synthetic graft by functionalizing the SMP with polymethacrylic acid (PMA) segments. One expects the electrostatic interaction between PMA and BMP-2 to facilitate better retention and more sustained release of the osteogenic growth factor to and from the bone graft.

For reported biodegradable SMP, melting points ($T_m$) were utilized exclusively as the transition temperatures ($T_{trans}$) to trigger the shape memory behavior of the SMP. In contrast, in our invention, glass transition ($T_g$) was used as the transition temperature trigger instead. Using $T_g$ as $T_{trans}$ has advantages.

Figure 10A:
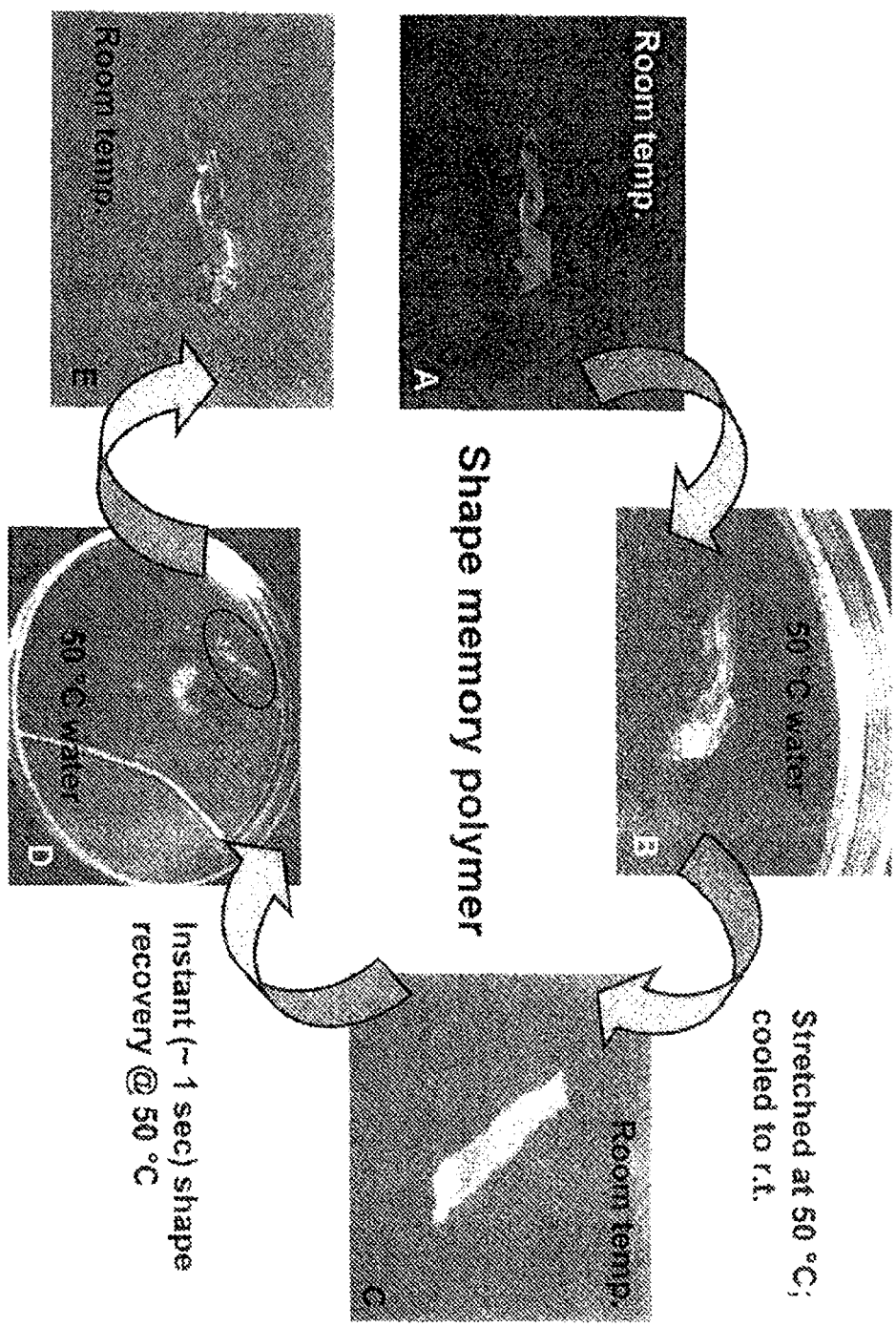
FIG. 10A shows shape memory of an embodiment of the invention.
Figure 10B:
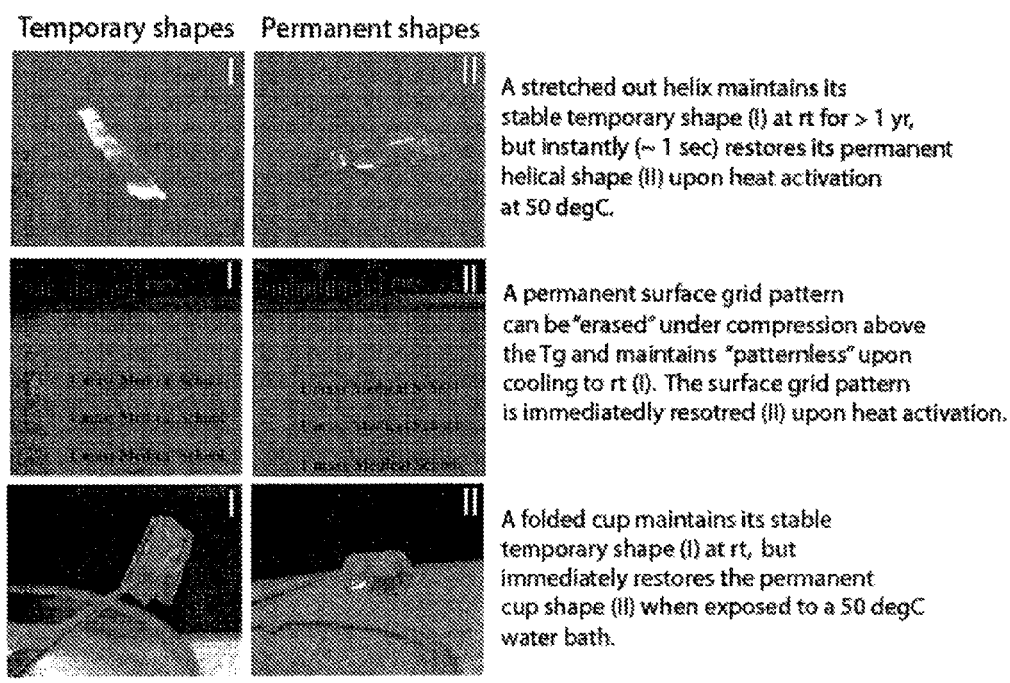
FIG. 10B shows the shape recovery from various stably held "temporary" shapes to pre-programmed "permanent" functional shapes upon thermal activation. All shape memory polymers shown are urethane-crosslinked POSS-$(PLA)_{20}$.
Figure 11A:
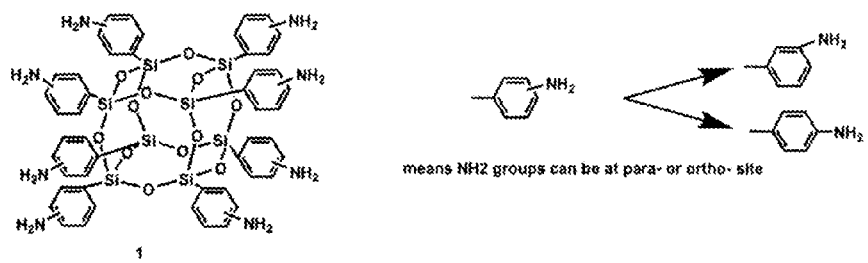
FIG. 11A illustrates a synthetic method for preparing embodiments of the invention.
Figure 11A:
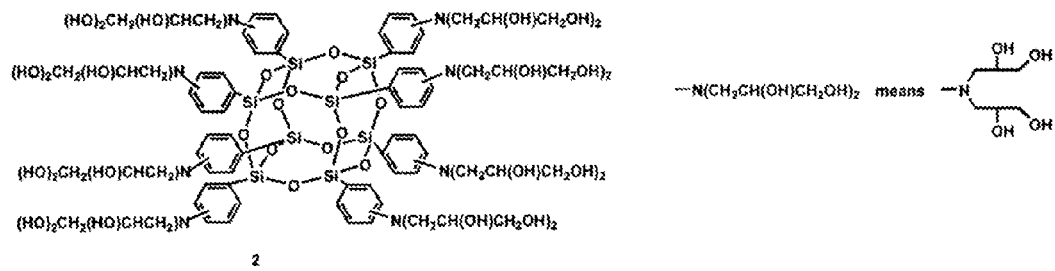
Figure 11B:
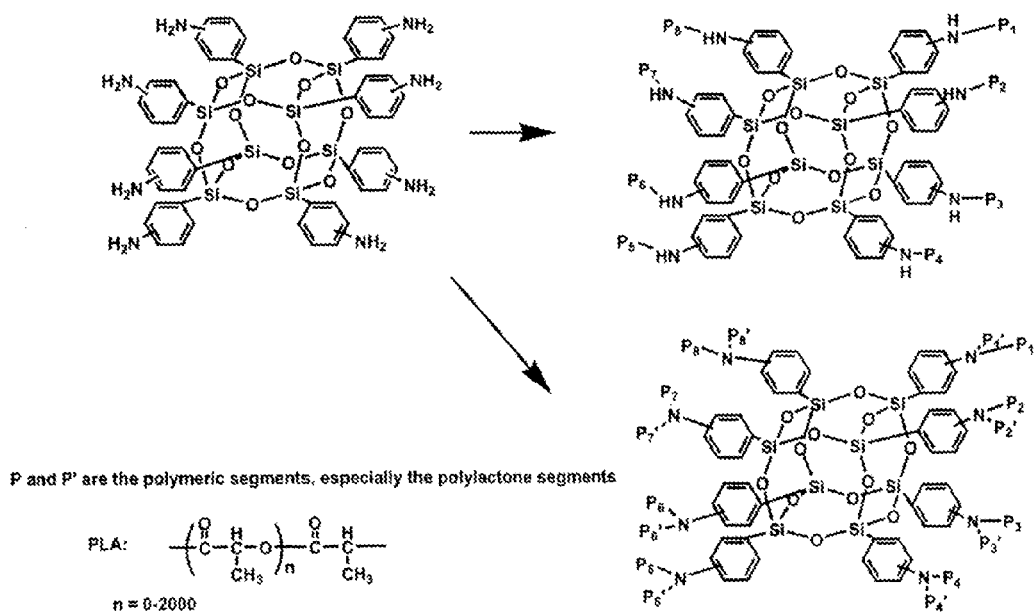
FIG. 11B illustrates a synthetic method for preparing embodiments of the invention.

First, crystallization and melting of polymeric chains (processes associated with $T_m$) are relatively slower processes than their glassy state freezing and activation (processes associated with $T_g$). Therefore, the shape fixation and recovery of a SMP system using Tm as its $T_{trans}$ takes longer time than that of the SMP using $T_g$ as $T_{trans}$. For instance, a piece of SMP with a thickness of 0.5 mm prepared in with embodiments of the invention can be fixed at its temporary shape in less than 1 second upon cooling to room temperature, and can fully recover to its original shape in less than 1 second upon raising the temperature to 50° C. (FIGS. 10A-B). Such an excellent shape memory effect within this physiologically relevant temperature range has not been achieved by any existing competitive SMPs.

Second, $T_g$ is more tunable than $T_m$. By increasing the polymeric chain lengths (e.g. via the increase of the monomer-to-POSS core feed ratio) or changing the copolymer compositions (e.g. changing the type and ratio of monomers co-polymerized), the $T_g$ value can be adjusted to the desired temperature range for specific applications. For example, the $T_g$ of crosslinked POSS-$(PLA_n)_8$ urethane can be tuned from 42.8° C. to 48° C. with the increase of the PLA chain length (attached to POSS core) from 10 to 40 (FIG. 7D).

Third, many previous polymers are semi-crystalline in nature, thus opaque in their appearances. The SMPs prepared in certain embodiments of the invention are transparent in appearance due to the fact that there are very little to no macro phase separation during crystallization (they are amorphous). This is a desirable feature for ophthalmic applications.

In addition, mechanical properties of SMPs prepared in certain embodiments of the invention are unique. The flexural modulus of our SMPs below the $T_{trans}$ is typically between 200 MPa and 20 GPa (FIGS. 7E-7I), within the range of those reported for human cortical bone. Given that the body temperature is 5-10° C. lower than the $T_{trans}$ of SMPs prepared in our invention, these materials may be used as smart bone grafts for load-bearing applications ranging from craniofacial (low weight-bearing), spinal fusion, to long bone segmental defects (high weight-bearing).

For example, U.S. Pat. No. 7,091,297, hereby incorporated by reference, discloses thermoplastic polymers with POSS diol units with a diisocyanate crosslinkers. However, for polymers disclosed in U.S. Pat. No. 7,091,297, incorporated herein by reference, only diisocyanates that help form crystalline domain can be used which is usually limited to MDI or HMDI; in addition significant annealing is required to achieve steady-state crystallinity. For certain preferred embodiments of the current invention, the material is a thermoset with star-shape polyester polyol. They are synthesized from multifunctional POSS and cyclic monomers. Many different types of cyclic monomers are available for the synthesis and virtually all kinds of diisocyanate can be used for crosslinking with excellent SMP effect upon preparation. In addition, the $T_g$ of the final crosslinked materials is adjustable by changing the arm length and arm composition and has mechanical properties of 200 MPa to 30 GPa. A $T_g$ slightly above body temperature is readily achievable. For polymers disclosed in U.S. Pat. No. 7,091,297, hereby incorporated by reference, the mechanical properties are less than several GPa and one is limited to the melting temperature of the selected polymeric diol. For example, the $T_m$ of polycaprolactone usually is around 60° C., far exceeding body temperature.

Siloxanes

The preparation of siloxanes, including silsesquioxanes and metallasiloxanes, are described in Purkayastha & Baruah Applied Organometallic Chemistry 2004, 18, 166-175. Silsesquioxane are compounds of an approximate formula of about $RSiO_{1.5}$, where R is any moiety but typically an alkyl, aryl, or substituted conjugate thereof. The compounds may assume a myriad of structures, including random, ladder, cage and partial cage structures (see FIG. 1B).

Figure 1A:
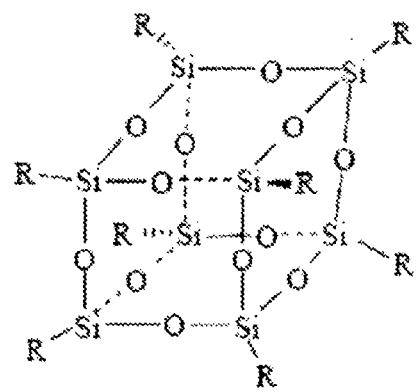
FIG. 1A shows an illustration of an embodiment of the invention wherein a POSS is functionalized with groups, R.
Figure 1B:
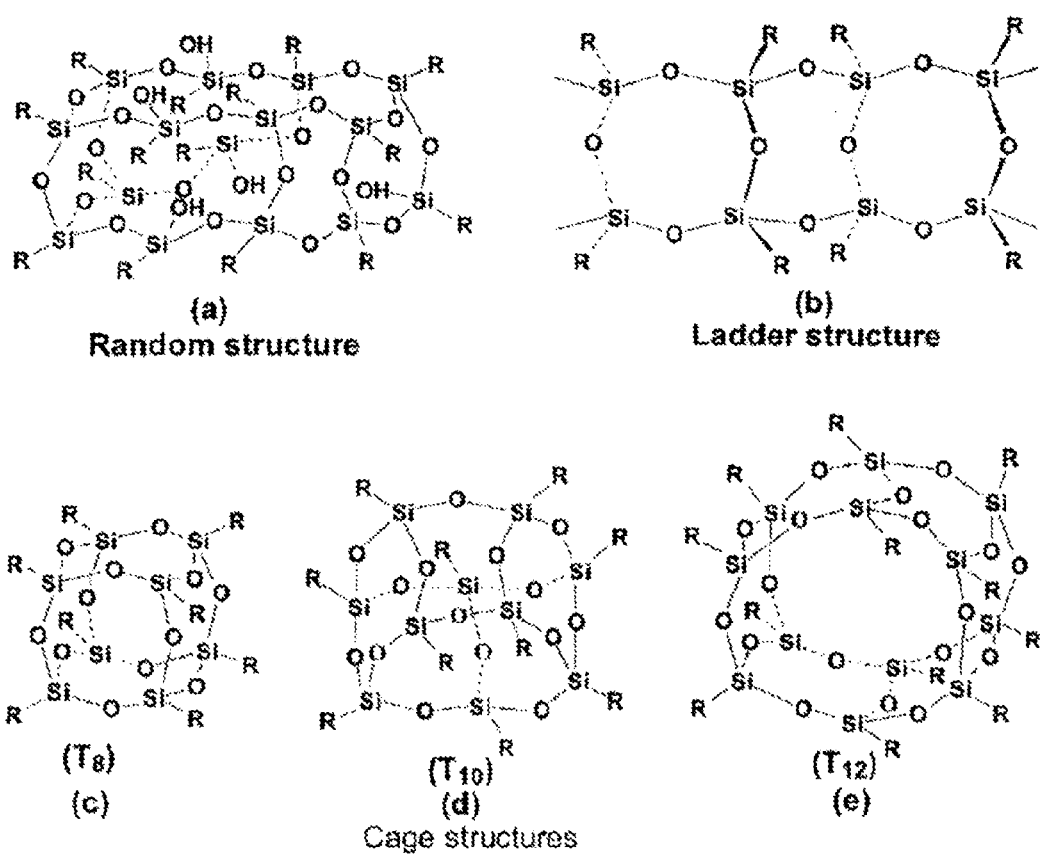
FIG. 1B shows an illustration of alternative POSS functionalized embodiments.
Figure 2:
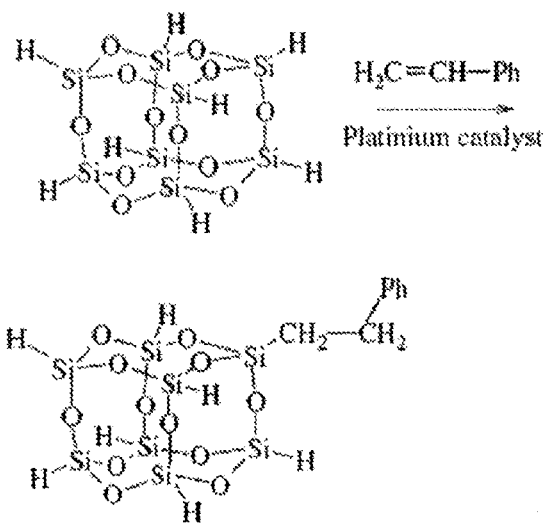
FIG. 2 shows a preferred method of making embodiments.

Silsesquioxanes are also sometimes termed ormosils (organically modified siloxanes). A preferred silsesquioxane is shown in FIG. 1A. To prepare monosubstituted silsesquioxane, there are several conventional synthetic routes. For example, the reaction of $HSiCl_3$ with $PhSiCl_3$ results in the formation of $PhH_7Si_8O_{12}$ via a co-hydrolysis reaction. A second route uses substitution reactions at a silicon center with the retention of the siloxane cage leads to structural modifications of silsesquioxane. For this reaction hydrosilylation is used as illustrated in FIG. 2.

These structures typically exhibit good insulating and permeability properties, allowing for their use as coatings for electronic and optical devices, semiconductors and liquid crystal display (LCD) devices, as well as gas separation membranes.

A variety of Polyhedral Oligomeric Silsesquioxanes (POSS) nanostructured chemicals have been prepared which contain one or more covalently bonded reactive functionalities that are suitable for polymerization, grafting, surface bonding, or other transformations. Lichtenhan, J. D. et al. U.S. Pat. No. 5,942,638 (1999); Lichtenhan, J. D. et al. Chem. Innovat. 1: 3 (2001), both of which are incorporated by reference. Monomers have recently become commercially available as solids or oils from Hybrid Plastics Company (http://www.hybridplastics.com/), Fountain Valley, Calif. A selection of POSS chemicals now exist that contain various combinations of nonreactive substituents and/or reactive functionalities. Thus, POSS nanostructured chemicals may be incorporated into common plastics via copolymerization, grafting, or blending as disclosed in Haddad et al. Polym. Prepr. 40: 496 (1999), incorporated herein by reference. The incorporation of POSS derivatives into polymeric materials can lead to enhancements as applied to a wide range of thermoplastics and thermoset systems. Ellsworth et al. Polym. News 24: 331 (1999), hereby incorporated by reference. POSS nanostructures have other use in catalyst supports and biomedical applications as scaffolds for drug delivery, imaging reagents, and combinatorial drug development.

Metallasiloxanes are siloxanes having some of the silicon atoms replaced by an appropriate metal. Incorporation of metal into a siloxane framework can lead to two and three-dimensional or linear networks. Metallasiloxane may be derived from silanediols, disilanol, silanetriols and trisilanols. For example, the transesterification reaction of $Ti(O-iPr)_4$ with sterically hindered silanediol $\{(t\text{-BuO}\text{---})_3 SiO\}_2Si(OH)_2$ gives cyclic siloxane of the following formula:

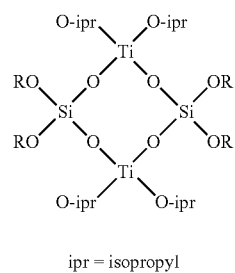

ipr = isopropyl

Similarly, cyclic dihalotitanasiloxanes $[t\text{-}Bu_2Si(O)OTiX_2]_2$ (X=Cl, Br, I) may be prepared by the direct reaction of titanium tetrachloride with $t\text{-}Bu_2Si(OH)_2$. Such compounds are made of eight-membered rings having composition $Ti_2Si_2O_4$. Both silicon and titanium atoms in the molecule exhibit regular tetrahedral geometry. Analogously, the corresponding zirconium compound $[t\text{-}Bu_2Si(O)OZrCl_2]_2$ may be prepared from the reaction between the dilithium salt of $t\text{-}Bu_2Si(OH)_2$ and $ZrCl_4$.

Cyclopentadienyl-substituted titanasiloxane $[t\text{-}Bu_2Si(O)OTiCpCl]_2$ may be prepared directly by the reaction of $CpTiCl_3$ with $t\text{-}Bu_2Si(OLi)_2$. The reaction of the silanediol $Ph_2Si(OH)_2$ with the zirconium amido derivative $Zr(NEt_2)_4$ leads to the formation of the dianonic tris-chelate metallasiloxane $[NEt_2H_2]_2[(Ph_4Si_2O_3)_3Zr]$. In the case of zirconocene, the central zirconium atom is coordinated by six oxygen atoms in a distorted octahedral geometry.

Figure 6:
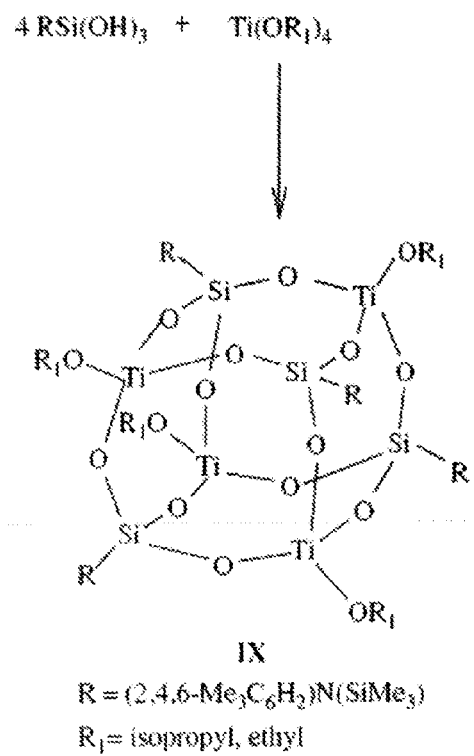
FIG. 6 shows alternative embodiments.

Disilanols may also be used as building blocks for a variety of metallasiloxanes. The disilanols are capable of chelating to form six-membered rings containing the central metal. The reactions lead to Group 4 metallasiloxanes from disilanols. In a similar manner, metallasiloxane derivatives of Group 5, Group 7, Group 9 and Main Group metals may be prepared from disilanols. Reactions of silanediol and disilanols with titanium halides or titanium amides give cyclic titanasiloxanes. Three-dimensional titanasiloxanes can be prepared by the reaction of the titanium amide with silanol or silanediol. Such reactions serve as a synthetic pathway for preparation of model compounds for titanium-doped zeolites. Cubic titanasiloxanes can be prepared by a single-step synthesis from the reaction of titanium orthoesters and silanetriols as illustrated in FIG. 6. In an analogous manner, the three-dimensional networks of aluminiumosiloxane, indiumsiloxane, galliumsiloxane, etc. may be prepared from the reaction of trisilanols and $MMe_3$ where M=Al, In, Ga, etc. In many of these networks, cubic metallasiloxanes, $M_4Si_4O_{12}$ polyhedrons, are present.

Synthesis of Polyhedral Oligomeric Silsesquioxanes

The preparation of oligomeric silsesquioxanes is generally described in Li et al. (2002) Journal of Inorganic and Organometallic Polymers 11, 123-154, incorporated herein by reference. Reactions leading to the formation of POSS may be characterized depending on the nature of the starting materials employed. One group includes the reactions giving rise to new Si—O—Si bonds with subsequent formation of the polyhedral cage framework. This class of reactions assembles polyhedral silsesquioxanes from monomers of the $XSiY_3$ type, where X is a chemically stable substituent (for example, $CH_3$, phenyl, or vinyl), and Y is a highly reactive substituent (for example, Cl, OH, or OR) as represented in Equation 1:

$$nXSiY_3 + 1.5nH_2O \rightarrow (XSiO_{1.5})_n + 3nHY \qquad \text{(Equation 1)}.$$

Alternatively, POSS can form from linear, cyclic, or polycyclic siloxanes that are derived from the XSiY$_3$-type monomers.

The second class of reactions involves the manipulation of the substituents at the silicon atom without affecting the silicon-oxygen skeleton of the molecule. A number of substituents may be appended to the silicon oxygen cages [R(SiO$_{1.5}$)]$_n$ (n=8, 10, 12, and larger). Such substituents include alcohols and phenols, alkoxysilanes, chlorosilanes, epoxides, esters, fluoroalkyls, halides, isocyanates, methacrylates and acrylates, alkyl and cycloalkyl groups, nitriles, norbornenyls, olefins, phosphines, silanes, silanols, and styrenes. Many of the reactive functionalities are suitable for polymerization or copolymerization of the specific POSS derivative with other monomers. In addition to substituents with reactive functional groups, nonreactive organic functionalities may be varied to influence the solubility and compatibilization of POSS nanostructured cages with polymers, biological systems, or surfaces.

Multifunctional POSS Synthesis

POSS (RSiO$_{1.5}$)$_n$, where R=H and n=8, 10, 12, 14, or 16, are structures generally formed by hydrolysis and condensation of trialkoxysilanes (HSi(OR)3) or trichlorosilanes (HSiCl$_3$). For example, (HSiO$_{1.5}$)$_n$, where n=8, 10, 12, 14, or 16, is prepared by hydrolysis of HSiCl$_3$ involving the addition of a benzene solution of HSiCl$_3$ to a mixture of benzene and SO$_3$-enriched sulfuric acid. The hydrolysis of trimethoxysilane may be carried out in cyclohexane-acetic acid in the presence of concentrated hydrochloric acid and leads to the octamer. The hydrolytic polycondensation of trifunctional monomers of type XSiY$_3$ leads to crosslinked three-dimensional networks and cis-syndiotactic (ladder-type) polymers, (XSiO$_{1.5}$)$_n$. With increasing amounts of solvent, however, the corresponding condensed polycyclosiloxanes, POSS, and their derivatives may be formed.

The reaction rate, the degree of oligomerization, and the yield of the polyhedral compounds formed under these conditions depend on several factors. For example, POSS cages where n=4 and 6 can be obtained in nonpolar or weakly polar solvents at 0 or 20° C. However, octa(phenylsilsesquioxane), Ph$_8$(SiO$_{1.5}$)$_8$, is more readily formed in benzene, nitrobenzene, benzyl alcohol, pyridine, or ethylene glycol dimethyl ether at high temperatures (e.g., 100° C.).

Figure 3:
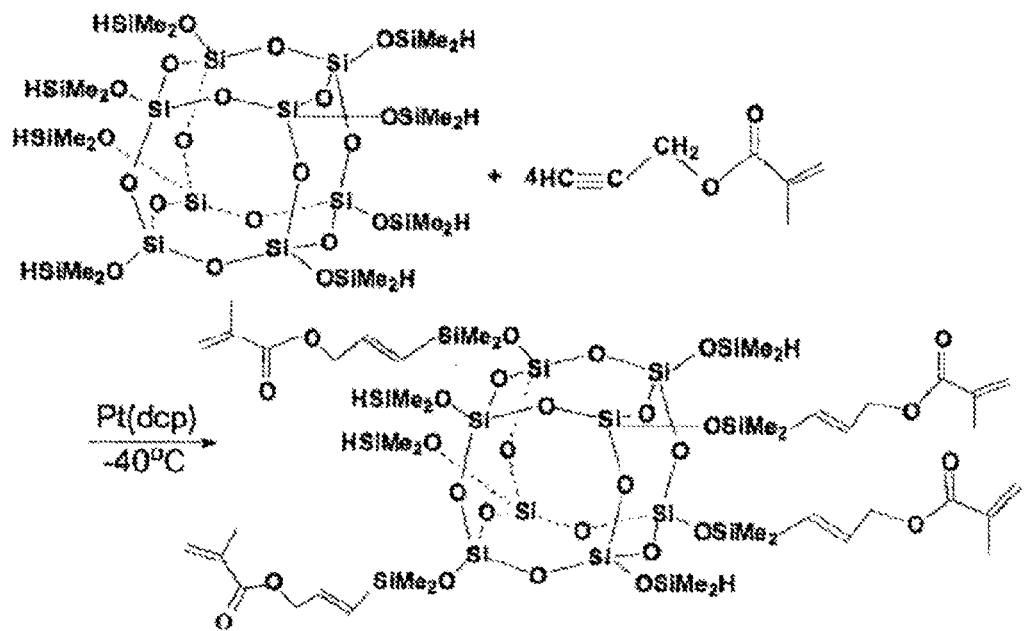
FIG. 3 shows alternative methods for making embodiments.

Multifunctional POSS derivatives can be made by the condensation of ROESi(OEt)$_3$, as described above, where ROE is a reactive group. This reaction produces an octa-functional POSS, R'$_8$(SiO$_{1.5}$)$_8$. Another approach involves functionalizing POSS cages that have already been formed. For example, this may be accomplished via Pt-catalyzed hydrosilylation of alkenes or alkynes with (HSiO$_{1.5}$)$_8$ and (HMe$_2$SiOSiO$_{1.5}$)$_8$ cages as shown in FIG. 3. Another example of the synthesis of multifunctional POSS derivatives is the hydrolytic condensation of modified aminosilanes as described in Fasce et al., *Macromolecules* 32: 4757 (1999), hereby incorporated by reference.

POSS Polymers and Copolymers

POSS units, which have been functionalized with various reactive organic groups, may be incorporated into existing polymer system through grafting or copolymerization. POSS homopolymers can also be synthesized. The incorporation of the POSS nanocluster cages into polymeric materials may result in improvements in polymer properties, including temperature and oxidation resistance, surface hardening and reductions in flammability. These shape-memory polymers, including but not limited to those disclosed in Examples V, VII and IX, may comprise materials suitable for both biomedical and non-biomedical applications.

Figure 4:
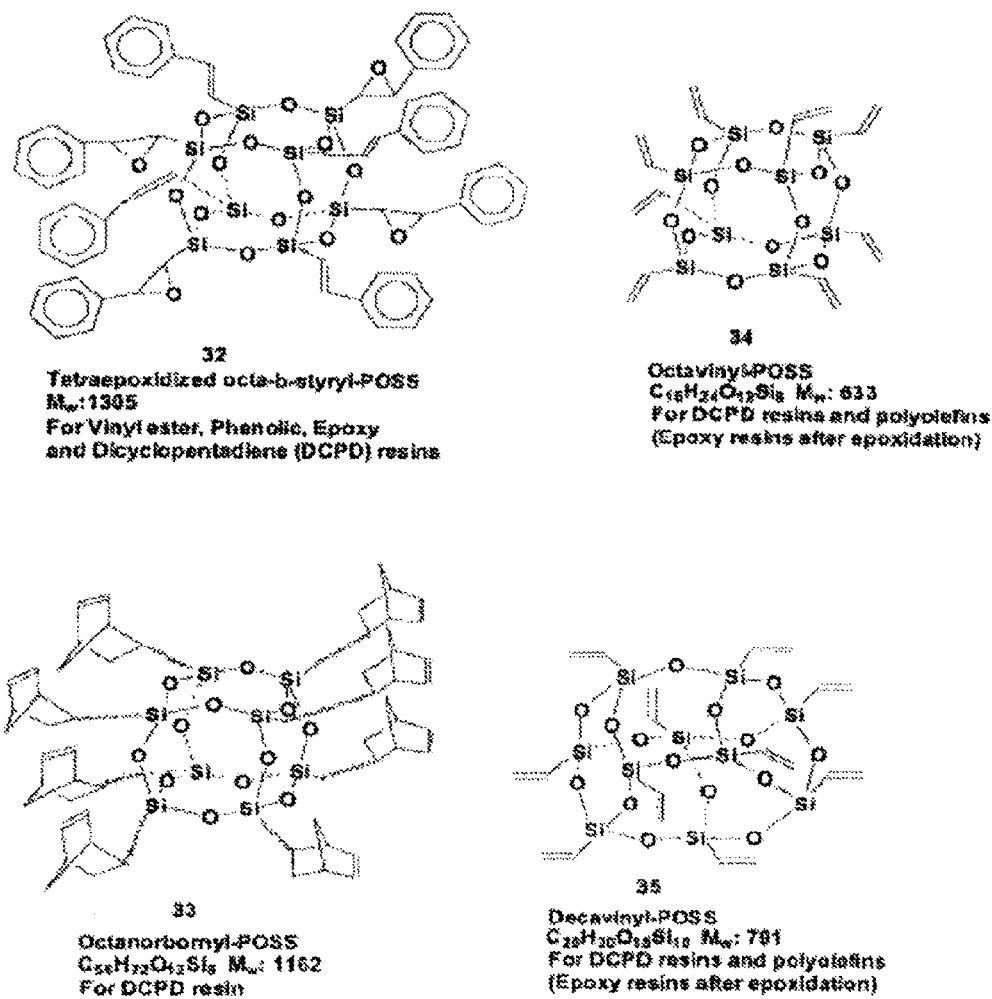
FIG. 4 shows illustrations of alternative embodiments.
Figure 4:
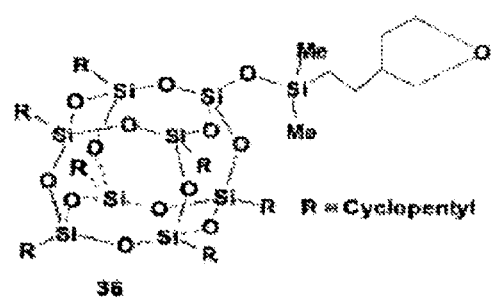
Figure 4:
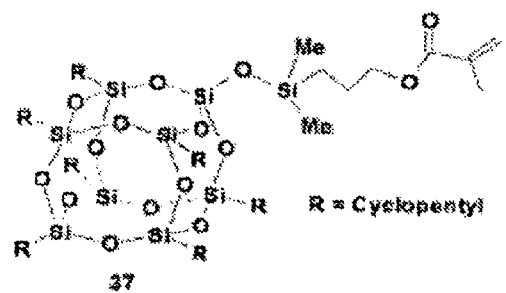
Figure 4:
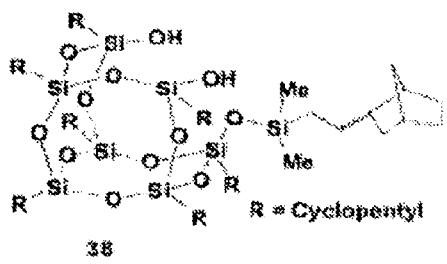
Figure 4:
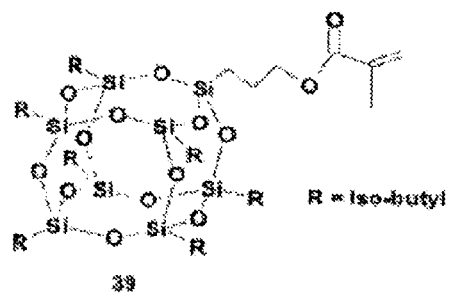

Different types of substituted POSS monomers may be chemically incorporated into resins. First, monofunctional monomers can be used. Alternatively, di- or polyfunctional POSS monomers can be used. Incorporating a monofunctional POSS monomer can actually lower the resulting resin's crosslink density if the amount of the monofunctional POSS monomers in the commercial resin employed is held constant. The POSS cages with organic functions attached to its corners have typical diameters of 1.2 to 1.5 nm. Therefore, each POSS monomer occupies a substantial volume. When that POSS monomer is monosubstituted, it cannot contribute to crosslinking. A 2 mol % loading of POSS in a resin might actually occupy 6 to 20 vol % of the resin, and this occupied volume contains no crosslinks. Therefore, the average crosslink density will be lowered. Conversely, when a polyfunctional POSS monomer is employed, several bonds can be formed from the POSS cage into the matrix, thereby making the POSS cage the center of a local crosslinked network. Some examples of monofunctional and polyfunctional POSS monomers are illustrated in FIG. 4 together with the types of resins into which they may be chemically incorporated. Epoxy, vinyl ester, phenolic, and dicyclopentadiene (DCPD) resins may be made in which various POSS macromers are chemically incorporated. Besides the applications in nano-reinforced polymeric materials, there are other applications for POSS molecules as a core for building new types of dendritic macromolecules.

Figure 5:
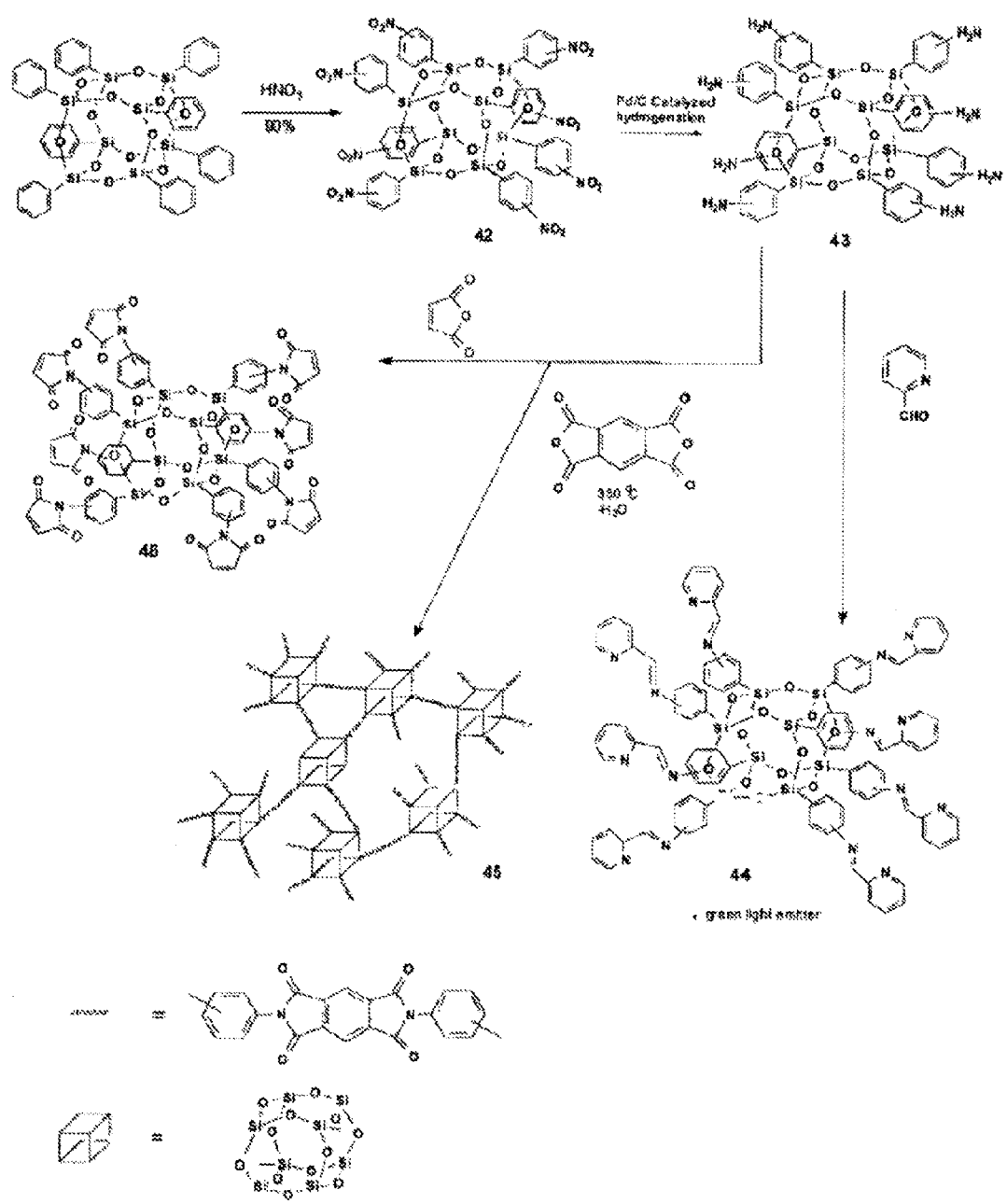
FIG. 5 shows alternative method for making embodiments.

As illustrated in FIG. 5, following the nitration of octaphenyl POSS 42 one may produce the octaaminophenyl POSS 43 by Pd/C-catalyzed hydrogenation of 42 as described in Tamaki et al., *JACS* 123, 12416-12417 (2001), incorporated herein by reference. One obtains a derivative, 44, by Schiff's base formation upon reaction of 43 with the ortho carboxaldehyde of pyridine. Furthermore, one uses the octaamino 43 with dialdehydes to make polyimide crosslinked networks. One reacts POSS 43 with maleic anhydride to make the octa-N-phenylmaleimide, 45, which could serve as a crosslinking agent in maleimide polymer chemistry.

Bone Implantation of POSS Polymeric and Copolymeric Composite Materials

A preferred embodiment of the present invention provides for the synthesis and use of composite materials. Biomineralized implant applications, e.g. the implantation of suitable biopolymers that contain inorganic minerals capable of being incorporated into native bone structure, offer significant improvements to subjects suffering from bone disorders and dysfunction. As described in US Patent Application Number 2004/0161444, incorporated herein by reference, inorganic minerals including but in no way limited to calcium hydroxyapatite, carbonate derivatized hydroxyapatite, and beta-tricalcium phosphate may be incorporated into biomaterials including but not limited to synthetic bone substrates. As discussed in Example X below, the present invention may be combined with said inorganic minerals to create materials and compositions suitable for use in biomedical applications. In a preferred embodiment, said inorganic minerals comprise 0.1%-90% by weight of the composite materials.

Bioimplantable Materials

A preferred embodiment of the present invention provides for its use as a supplement for bones that are compromised or at risk for compromise as well as tissue samples or systems that are compromised or at risk for compromise. As described in U.S. Pat. No. 6,767,928, hereby incorporated by reference, porous polymeric materials suitable for growth factor release, cellular attachment and tissue growth have been described. The present invention will find utility in these aforementioned applications due to its thermally responsive shape changes and pore recovery properties. The present invention may be further modified by attaching polymeric domains comprising multiple polymers such as block copolymers to the POSS core unit or units comprising the present invention. Such functional groups may be incorporated by methodologies that are well known to persons of ordinary skill in the art. While the present invention is in no way limited to the synthetic methods used to generate the aforementioned modified POSS domains, preferred methods include reversible addition fragmentation transfer (RAFT) and atom transfer radical polymerization (ATRP).

DEFINITIONS

As used herein, a "material" means a physical substance preferably a solid, but it is not intended to be limited to a solid material. It is also not intended to be limited to those substances that are actually used in the manufacture or production of a device.

As used herein, a material that exhibits "shape memory" refers to a material that will, without the prevention of another outside physical barrier, change to a previously adapted shape upon exposure to a certain temperature. Shape memory materials may have different kinds of shape memory effects. The two common memory effects are the one-way and two-way shape memory. With the one-way effect, cooling from high temperatures does not cause a shape change. One can physically deform the material. Subsequent heating transforms the material into its original shape. The two-way shape memory effect is the effect that the material remembers two different shapes—one at low temperatures, and one at the high temperature shape—preferably without the application of an external force (intrinsic two-way effect).

The term "conjugate", as used herein, refers to any compound that has been formed by the joining of two or more moieties.

A "moiety" or "group" is any type of molecular arrangement designated by formula, chemical name, or structure. Within the context of certain embodiments, a conjugate is said to comprise one or more moieties or chemical groups. This means that the formula of the moiety is substituted at some place in order to be joined and be a part of the molecular arrangement of the conjugate. Although moieties may be directly covalently joined, it is not intended that the joining of two or more moieties must be directly to each other. A linking group, crosslinking group, or joining group refers any molecular arrangement that will connect the moieties by covalent bonds such as, but are not limited to, one or more amide group(s), may join the moieties. Additionally, although the conjugate may be unsubstituted, the conjugate may have a variety of additional substituents connected to the linking groups and/or connected to the moieties. Siloxanes moieties are molecular arrangements containing silicon-oxygen bonds. Preferably, within certain embodiments, the siloxane moieties are caged structures.

Figure 8A:
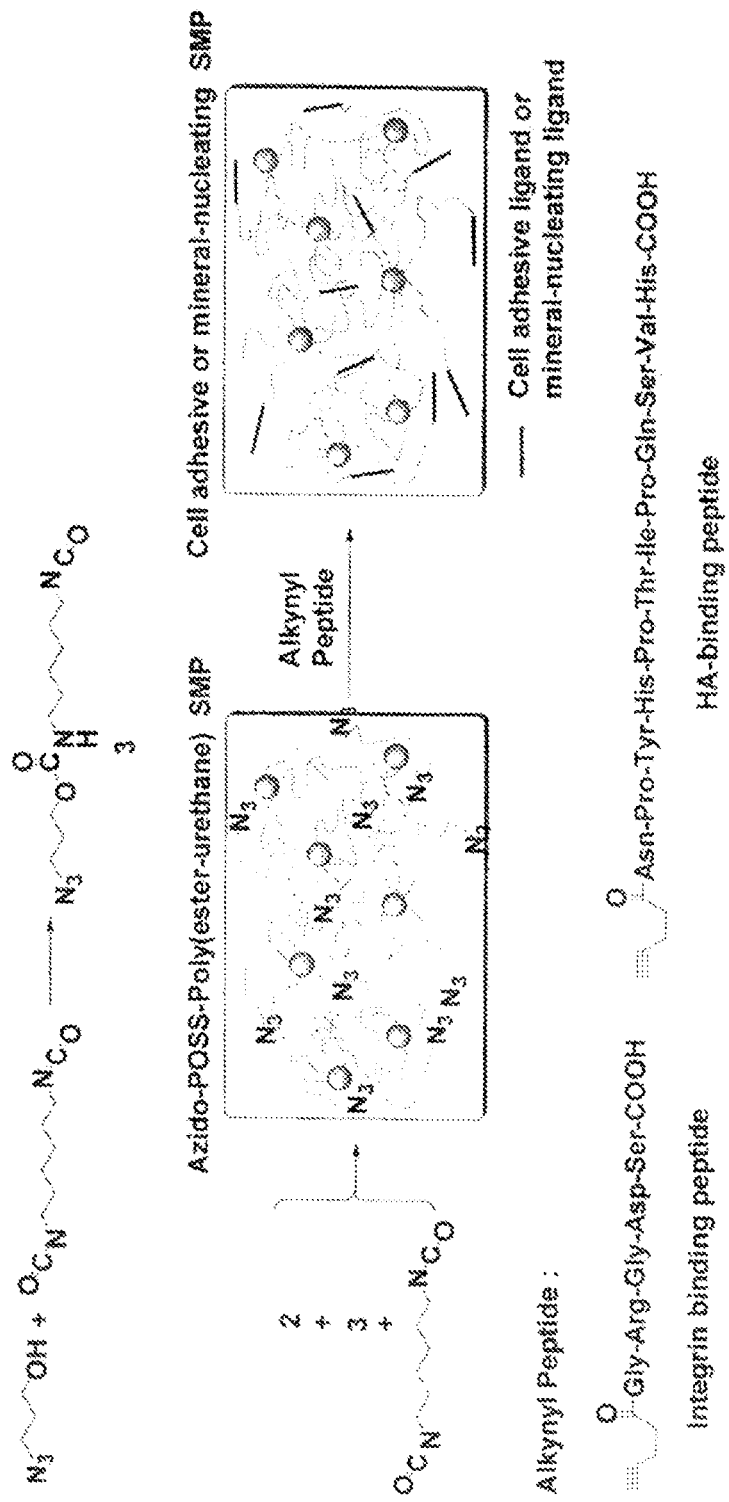
FIG. 8A illustrates a synthetic method for attaching bioactive peptides of preferred embodiments, where the mineral nucleating peptide is HA-binding peptide (SEQ ID No.: 1) and the cell adhesive ligand is (SEQ ID No.: 2).
Figure 8B:
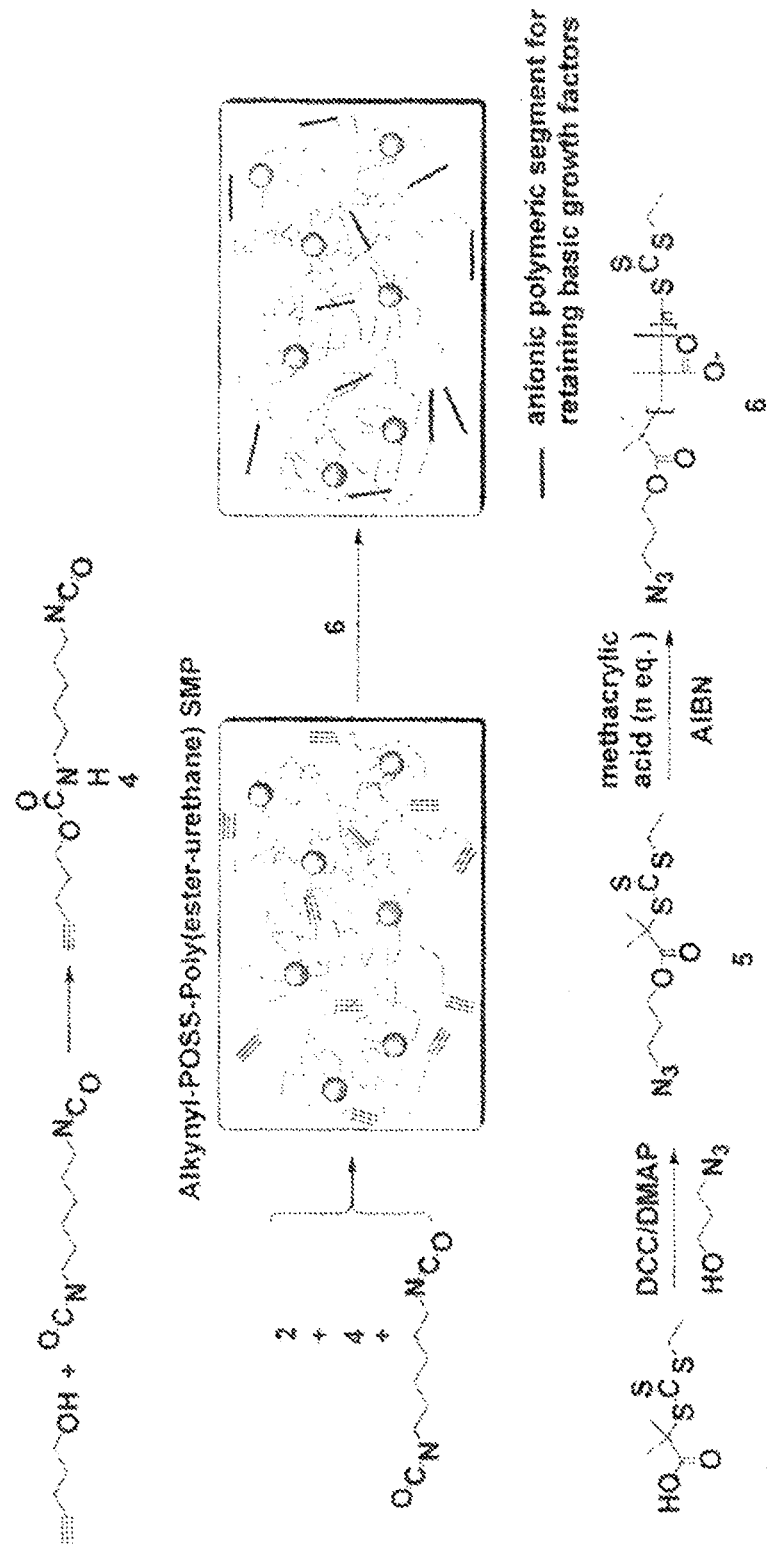
FIG. 8B illustrates a synthetic method for attaching anionic growth factor-retention domains to the POSS-poly(ester-urethane) SMP.

A "polymer" or "polymer group" means a chemical species or group made up of repeatedly linked moieties. Within certain embodiments, it is preferred that the number repeating moieties is three or more or greater than 10. The linked moieties may be identical in structure or may have variation of moiety structure. In a preferred embodiment, the polymer is made up of moieties linked by ester groups, i.e., polyester. Polyesters include polymer architecture obtained through stereoselective polymerizations. Polylactone means a polyester of any cyclic diester preferably the glycolide the diester of glycolic acid, lactide the diester of 2-hydroxypropionic acid, ethylglycolide, hexylglycolide, and isobutylglycolide which can be produced in chiral and racemic forms by, e.g., fermentation of corn. Metal alkoxide catalysts may be used for the ring-opening polymerization (ROP) of lactones. In the presence of chiral catalysts, each catalyst enantiomer preferentially polymerizes one lactone stereoisomer to give polymer chains with isotactic domains. A "monomeric polymer" or "homopolymer" is a polymer that contains the same repeating, asymmetric subunit. A "copolymer" is a polymer that is derived from two or more types of monomeric species, i.e. two or more different chemical asymmetric subunits. "Block copolymers" are polymers comprised of two or more species of polymer subunits linked by covalent bonds. FIGS. 8E and 8H provide for suitable block copolymers that may be incorporated into the present invention.

The term "substituted", as used herein, means at least one hydrogen atom of a molecular arrangement is replaced with a substituent. In the case of an oxo substituent ("=O"), two hydrogen atoms are replaced. When substituted, one or more of the groups below are "substituents." Substituents include, but are not limited to, halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle, and heterocyclealkyl, as well as, $-NR_aR_b$, $-NR_aC(=O)R_b$, $-NR_aC(=O)NR_aNR_b$, $-NR_aC(=O)OR_b$ $-NR_aSO_2R_b$, $-C(=O)R_a$, $C(=O)OR_a$, $-C(=O)NR_aR_b$, $-OC(=O)NR_aR_b$, $-OR_a$, $-SR_a$, $-SOR_a$, $-S(=O)_2R_a$, $-OS(=O)_2R_a$ and $-S(=O)_2OR_a$. In addition, the above substituents may be further substituted with one or more of the above substituents, such that the substituent comprises a substituted alky, substituted aryl, substituted arylalkyl, substituted heterocycle, or substituted heterocyclealkyl. $R_a$ and $R_b$ in this context may be the same or different and, independently, hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl.

The term "unsubstituted", as used herein, refers to any compound does not contain extra substituents attached to the compound. An unsubstituted compound refers to the chemical makeup of the compound without extra substituents, e.g., the compound does not contain protecting group(s). For example, unsubstituted proline is a proline amino acid even though the amino group of proline may be considered disubstituted with alkyl groups.

The term "alkyl", as used herein, means any straight chain or branched, non-cyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms. Representative saturated straight chain alkyls include, but are not limited to, methyl, ethyl, n-propyl, n-butyl, n-pentyl, n-hexyl, n-septyl, n-octyl, n-nonyl, and the like; while saturated branched alkyls include, but are not limited to, isopropyl, sec-butyl, isobutyl, tert-butyl, isopentyl, and the like. Cyclic alkyls may be obtained by joining two alkyl groups bound to the same atom or by joining two alkyl groups each bound to adjoining atoms. Representative saturated cyclic alkyls include, but are not limited to, cyclopropyl, cyclobutyl, cyclopentyl, cyclohexyl, and the like; while unsaturated cyclic alkyls include, but are not limited to, cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include, but are not limited to, acetylenyl, propynyl, 1-butynyl, 2-butynyl, 1-pentynyl, 2-pentynyl, 3-methyl-1-butynyl, and the like.

The term "aryl", as used herein, means any aromatic carbocyclic moiety such as, but not limited to, phenyl or naphthyl.

The term "arylalkyl", as used herein, means any alkyl having at least one alkyl hydrogen atoms replaced with an aryl moiety, such as benzyl, but not limited to, —(CH$_2$)$_2$phenyl, —(CH$_2$)$_3$phenyl, —CH(phenyl)$_2$, and the like.

The term "halogen", as used herein, refers to any fluoro, chloro, bromo, or iodo moiety.

The term "haloalkyl", as used herein, refers to any alkyl having at least one hydrogen atom replaced with halogen, such as trifluoromethyl, and the like.

The term "heteroaryl", as used herein, refers to any aromatic heterocycle ring of 5- to 10 members and having at least one heteroatom selected from nitrogen, oxygen and sulfur, and containing at least 1 carbon atom, including, but not limited to, both mono- and bicyclic ring systems. Representative heteroaryls include, but are not limited to, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, or quinazolinyl.

The term "heteroarylalkyl", as used herein, means any alkyl having at least one alkyl hydrogen atom replaced with a heteroaryl moiety, such as —CH$_2$pyridinyl, —CH$_2$pyrimidinyl, and the like.

The term "heterocycle" or "heterocyclic ring", as used herein, means any 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles may include heteroaryls exemplified by those defined above. Thus, in addition to the heteroaryls listed above, heterocycles may also include, but are not limited to, morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heterocyclealkyl", as used herein, means any alkyl having at least one alkyl hydrogen atom replaced with a heterocycle, such as —CH$_2$morpholinyl, and the like.

The term "homocycle" or "homocyclic ring", as used herein, means any saturated or unsaturated (but not aromatic) carbocyclic ring containing from 3-7 carbon atoms, such as, but not limited to, cyclopropane, cyclobutane, cyclopentane, cyclohexane, cycloheptane, cyclohexene, and the like.

The term "alkylamino", as used herein, means at least one alkyl moiety attached through a nitrogen bridge (i.e., —N-(alkyl)$_N$, such as a dialkylamino)) including, but not limited to, methylamino, ethylamino, dimethylamino, diethylamino, and the like.

The term "alkyloxy", as used herein, means any alkyl moiety attached through an oxygen bridge (i.e., —O-alkyl) such as, but not limited to, methoxy, ethoxy, and the like.

The term "alkylthio", as used herein, means any alkyl moiety attached through a sulfur bridge (i.e., —S-alkyl) such as, but not limited to, methylthio, ethylthio, and the like The term "alkenyl" means a unbranched or branched hydrocarbon chain having one or more double bonds therein. The double bond of an alkenyl group can be unconjugated or conjugated to another unsaturated group. Suitable alkenyl groups include, but are not limited to (C$_2$-C$_8$)alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

The term "alkynyl" means unbranched or branched hydrocarbon chain having one or more triple bonds therein. The triple bond of an alkynyl group can be unconjugated or conjugated to another unsaturated group. Suitable alkynyl groups include, but are not limited to, (C$_2$-C$_8$)alkynyl groups, such as ethynyl, propynyl, butynyl, pentynyl, hexynyl, methylpropynyl, 4-methyl-1-butynyl, 4-propyl-2-pentynyl-, and 4-butyl-2-hexynyl. An alkynyl group can be unsubstituted or substituted with one or two suitable substituents The term "salts", as used herein, refers to any salt that complexes with identified compounds contained herein. Examples of such salts include, but are not limited to, acid addition salts formed with inorganic acids (e.g. hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Salt compounds can also be administered as pharmaceutically acceptable quaternary salts known by a person skilled in the art, which specifically include the quaternary ammonium salts of the formula —NR,R',R"$^+$Z$^-$, wherein R, R', R" is independently hydrogen, alkyl, or benzyl, and Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate). Salt compounds can also be administered as pharmaceutically acceptable pyridine cation salts having a substituted or unsubstituted partial formula:

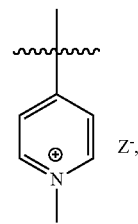

wherein Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

As used herein, reactive groups refer to nucleophiles, electrophiles, or radically active groups, i.e., groups that react in the presence of radicals. A nucleophile is a moeity that forms a chemical bond to its reaction partner (the electrophile) by donating both bonding electrons. Electrophile accept these electrons. Nucleophiles may take part in nucleophilic substitution, whereby a nucleophile becomes attracted to a full or partial positive charge on an element and displaces the group it is bonded to. Alternatively nucleophiles may take part in substitution of carbonyl group. Carboxylic acids are often made electrophilic by creating succinyl esters and reacting these esters with aminoalkyls to form amides. Other common nucleophilic groups are thiolalkyls, hydroxylalkys, primary and secondary amines, and carbon nucleophiles such as enols and alkyl metal complexes. Other preferred methods of ligating proteins, oligosaccharides and cells using reactive groups are disclosed in Lemieux & Bertozzi, *Trends in Biotechnology* 16 (12): 506-513 (1998), incorporated herein by reference. In yet another preferred method, one provides reactive groups for the Staudinger ligation, i.e., "click chemistry" with an azide comprising moiety and an alkynyl reactive groups to form triazoles. Micheal additions of a carbon nucleophile enolate with an electrophilic carbonyl, or the Schiff base formation of a nucleophilic primary or secondary amine with an aldehyde or ketone may also be utilized. Other methods of bioconjugation are provided in Hang & Bertozzi, *Accounts of Chemical Research* 34, 727-73 (2001) and Kiick et al., *Proc. Natl. Acad. Sci. USA* 99, 2007-2010 (2002), both of which are incorporated by reference.

As used herein, a crosslinking refers to joining moieties together by covalent bonding using a crosslinking agent, i.e., forming a linking group, or by the radical polymerization of monomers such as, but not limited to methacrylates, methacrylamides, acrylates, or acrylamides. In some embodiment, the linking groups are grown to the end of the polymer arms. In preferred embodiments, siloxane-polymers conjugates have alkenyl groups and are crosslinked by radical polymerization the absence or presence of other molecules that contain alkenyl groups, such as, but not limited to, methacrylates, methacrylamides, acrylates, or acrylamides and crosslinkers and radical initiators.

As used herein, a radical refers are species with a single, unpaired electron. Radical species can be electrically neutral, but it is not intended that the term be limited to electrically neutral species, in which case they are referred to as free radicals. Pairs of electrically neutral radicals may be formed via homolytic bond breakage. Molecular chlorine, $Cl_2$, forms chlorine radicals (Cl.) upon heating. Similarly peroxides form oxygen radicals and per-esters fragment to acyl radicals, which may decompose to lose carbon dioxide to give carbon radicals. Azo compounds eject nitrogen to give a pair of carbon radicals. Many polymers may be made by the chain radical addition of substituted alkenyl moieties with radicals.

The term "biocompatible", as used herein, refers to any material does not illicit a substantial detrimental response in the host. There is always concern, when a foreign object is introduced into a living body, that the object will induce an immune reaction, such as an inflammatory response that will have negative effects on the host. In the context of this invention, biocompatibility is evaluated according to the application for which it was designed: for example; a bandage is regarded a biocompatible with the skin, whereas an implanted medical device is regarded as biocompatible with the internal tissues of the body. Preferably, biocompatible materials include, but are not limited to, biodegradable and biostable materials. A substantial detrimental response has not occurred if an implant comprising the material is in close association to its implant site within the host animal and the response is better than a tissue response recognized and established as suitable from a materials provided in an ASTM. ASTM subcommittee F04.16 on Biocompatibility Test Methods has developed biocompatibility standards for medical and surgical materials and devices. For example, materials that are to be used in contact with the blood stream must be composed of materials that meet hemocompatibilty standards. One of these tests is for damage to red blood cells, which can result in hemolysis, that is, rupturing of the cells, as described in F 756, Practice for Assessment of Hemolytic Properties of Materials, incorporated herein by reference.

As used herein, a "bioactive substance" refers to any of a variety of chemical moieties and that binds with a biomolecule such as, but not limited to, peptides, proteins, enzymes, receptors, substrates, lipids, antibodies, antigens, and nucleic acids. In certain preferred embodiments, the bioactive substance is a biomolecule but it not intended that the bioactive substance be limited to biomolecules. In other preferred embodiments, the bioactive substances provide hydrophobic, hydrophilic or electrostatic interactions, such as polycarboxylic acids that are anionic at physiological pH. In other preferred embodiment, the alkaline growth factors (with isoelectric point above 7) are retained via favorable electrostatic interactions by the polycarboxylates, and subsequently released in a controlled and sustained manner.

For materials herein, $T_g$, glass temperature, refers to the temperature at which the Gibbs free energy is such that the activation energy for the cooperative movement of a substantial number of elements of the polymer is exceeded. $T_g$ is typically experimentally determined by measuring the stiffness of the material verses the temperature, i.e., as one increased the temperature, $T_g$ has been reached when the stiffness stays substantially the same, plateaus, for a while, until the material melts, $T_m$.

EXAMPLES

The following examples are provided in order to demonstrate and further illustrate certain preferred embodiments and aspects of the present invention and are not to be construed as limiting the scope thereof.

Example I

Synthetic Methods and Characterization of Some Embodiments of the Present Invention Silicon-based nanoparticles are chosen as the structural and mechanical anchor for grafting block copolymers to generate star-shaped macromer building blocks of the synthetic bone substitute. As described in FIG. 7A, octakis(dimethylsiloxy) octasilsesquioxane (POSS) was hydrosilylated by allyl alcohol catalyzed by platinum divinyltetramethyldisiloxane, Pt(dvs), to form a octahedral hydroxylated POSS core as shown in FIG. 7A (1) following precipitation in acetone/ether and repeated washing with toluene (90% yield). Grafting of biodegradable polylactide (PLA) arms to 1 was achieved by ring opening polymerization (ROP) of cyclic racemic lactide (5, 10 or 20 eq. relative to the number of OH's in 1). The polymerization was catalyzed by stannous octoate (0.2 wt %), which was added to the optically clear melt of lactides at 115° C. under nitrogen. Macromers 2 (POSS-(PLA$_n$)$_8$, wherein n=10, 20 and 40), were obtained in >90% yield. $^1$H NMR (FIG. 7B) revealed expected increase of proton intensity within the PLA repeat (elements e and f of the disclosed NMR spectra) relative to those of the POSS core (a, b, c and d of the disclosed NMR spectra) as the polyester chain grew from n=10 to n=20. The varying PLA lengths should result in different in vivo biodegradation rates. Molecular weight distribution of 2 (FIG. 7C) was determined by gel permeation chromatography (GPC) using two 5-mm PLGel MiniMIX-D column (Polymer Labs) in THF on a Varian HPLC system equipped with an evaporative light scattering detector. The system was calibrated using polystyrene standards and a Polymer Labs Galaxie Cirrus AIA GPC Software.

Figure 8C:
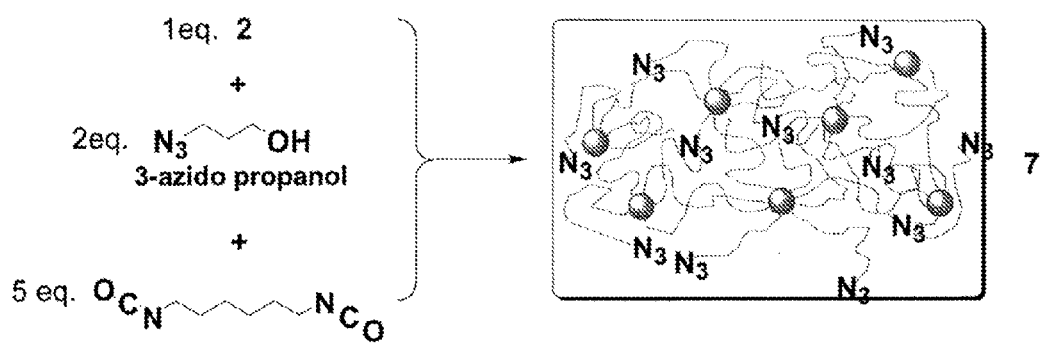
FIG. 8C illustrates a synthetic method for preparing embodiments of the invention.
Figure 8D:
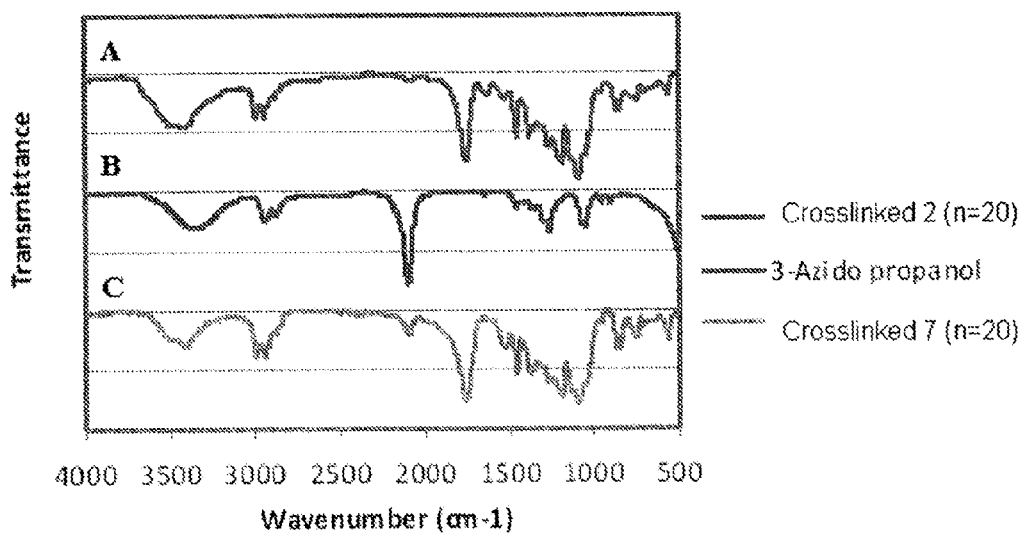
FIG. 8D shows the Fourier transform infrared (FTIR) spectrum of crosslinked macromers of the present invention and 3-azido propanol (FIG. 8C).
Figure 8E:
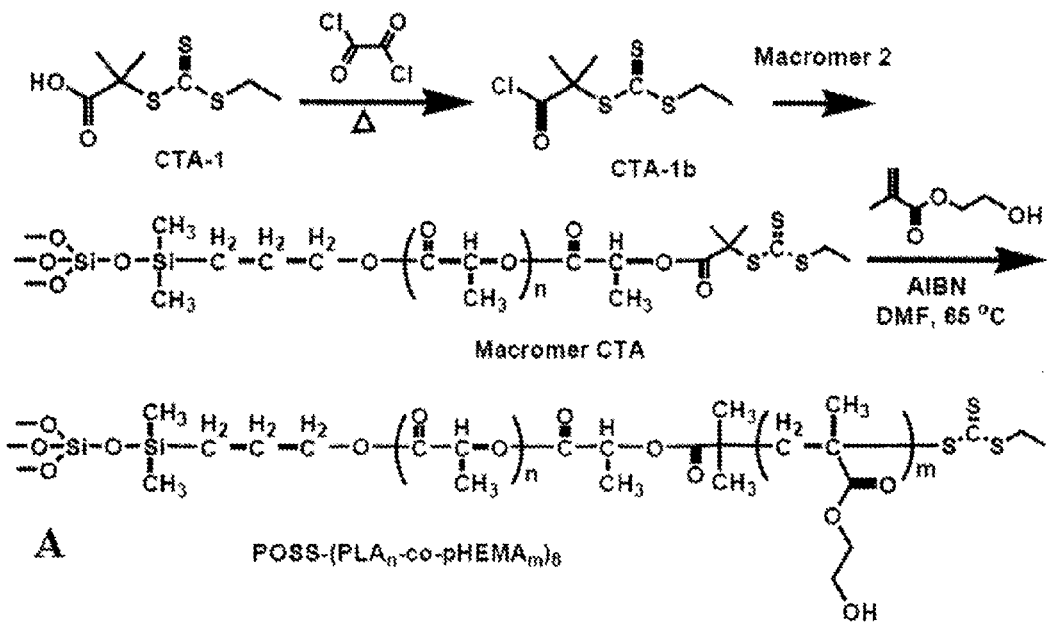
FIG. 8E illustrates a synthetic route for the attachment of CTA-1 to macromer 2 and the subsequent grafting of pHEMA to the macromer CTA by RAFT polymerization.
Figure 8F:
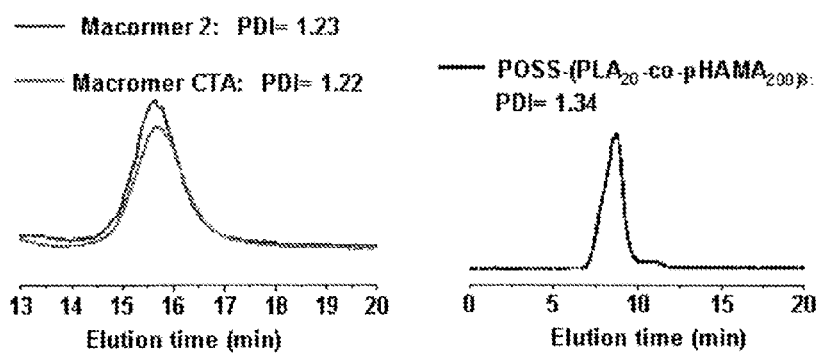
FIG. 8F shows data of GPC characterization of macromer 2, macromer CTA and the POSS-$(PLA_n$-co-pHEMA$_m)_8$ obtained via RAFT (n=20, m=200). Polydispersity ($M_w/M_n$) was determined using a PLGel Mixed-D column on a Varian HPLC equipped with an evaporative light scattering detector.
Figure 8G:
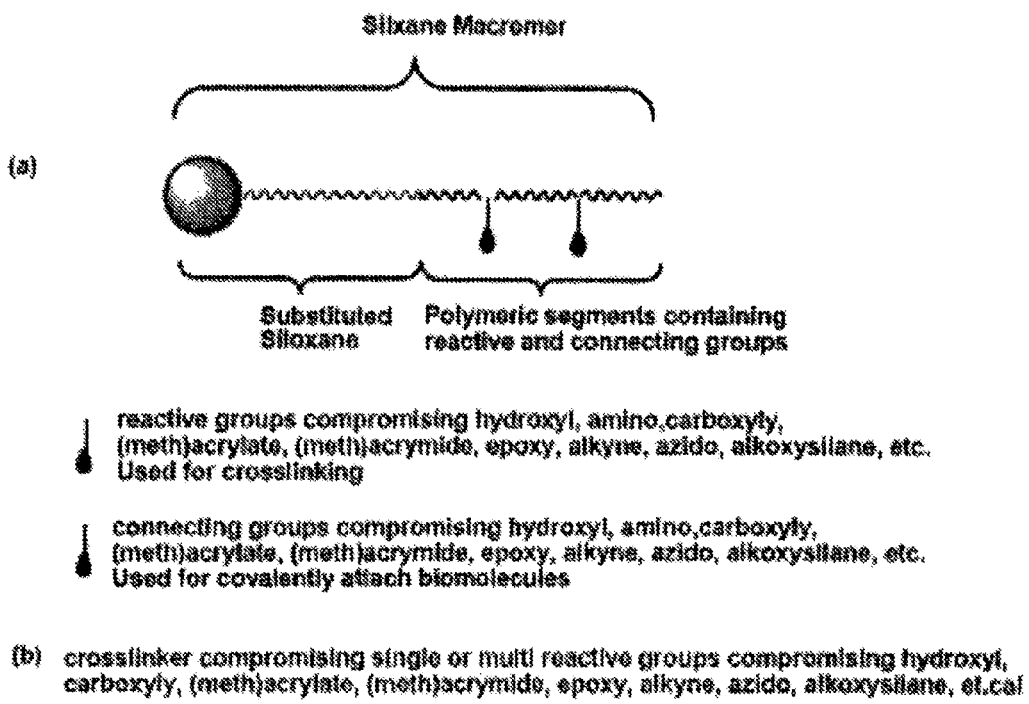
FIG. 8G illustrates one of the strategies of making functional shape memory polymers as an embodiment of the invention.
Figure 9A:
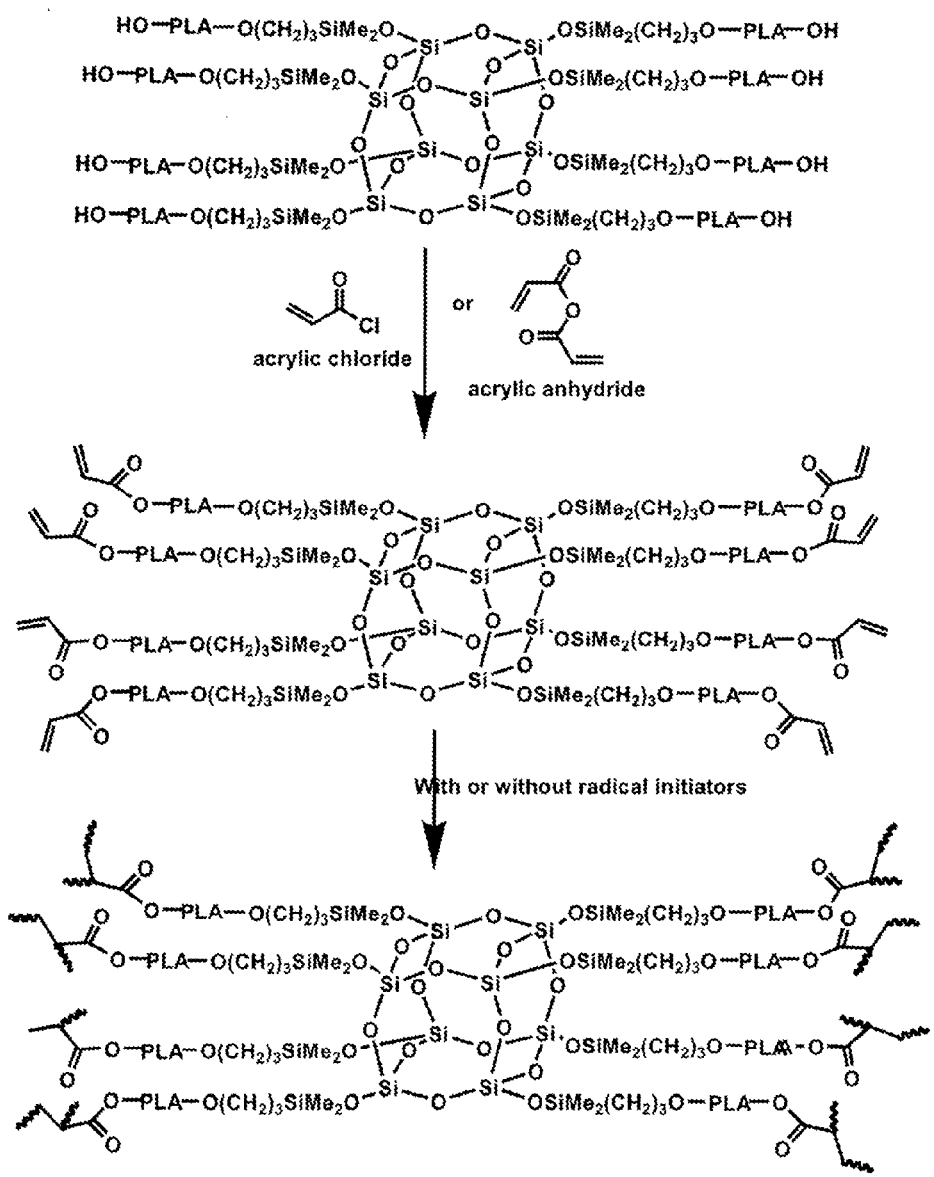
FIG. 9A illustrates a synthetic method for making embodiments of the invention.
Figure 9B:
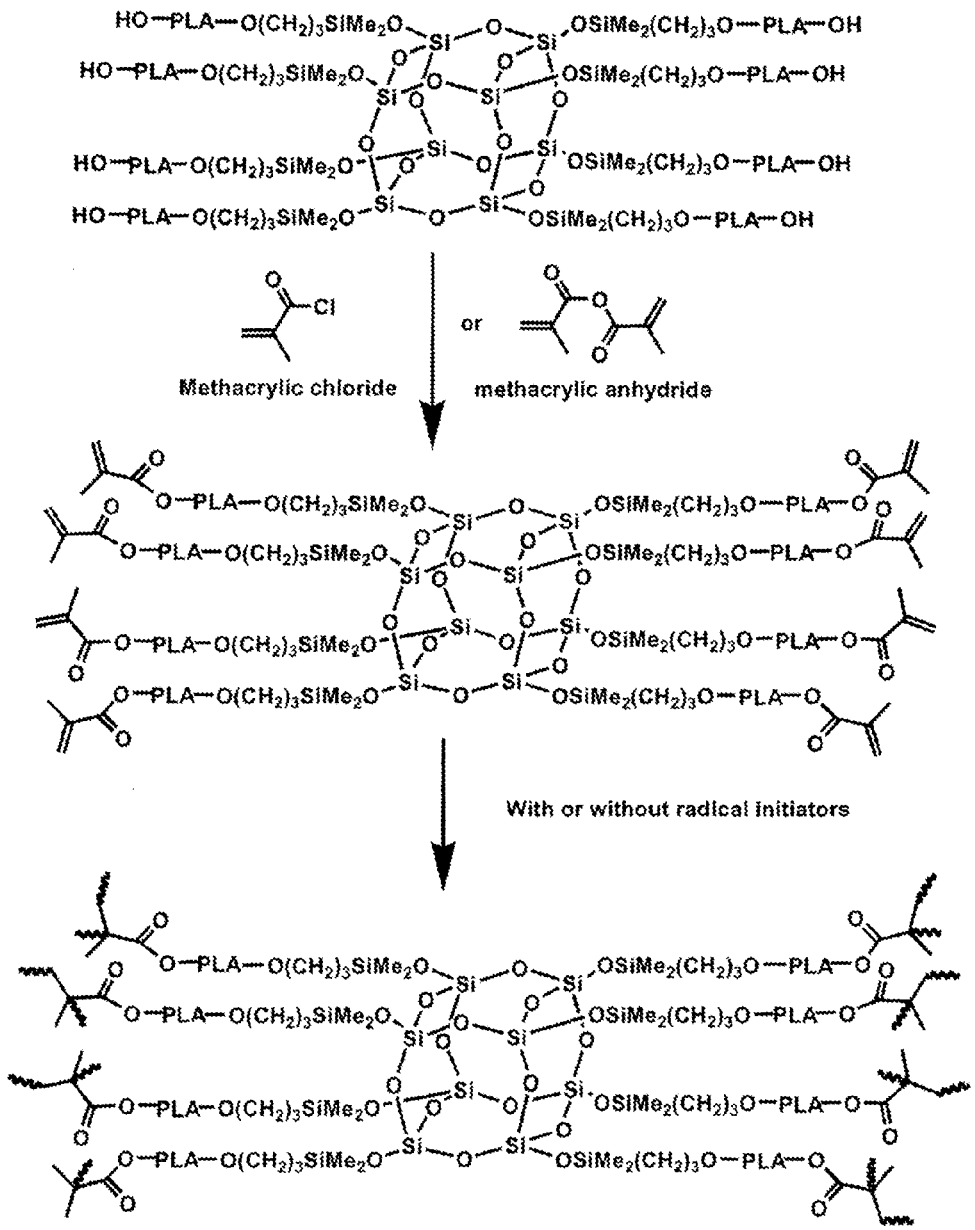
FIG. 9B illustrates another synthetic method for making embodiments of the invention.

Additional methods for synthesizing the functional shape memory polymers and macromer structures of the present invention are illustrated in FIGS. 8G and 8H.

Example II

Crosslinking of Biodegradable POSS-(PLA$_n$)$_8$ and Characterization of their Thermal and Mechanical Properties

Star-shaped macromer 2 (FIG. 7A) was crosslinked by diisocyanates to form the SMP which were cast into desirable "permanent" shapes, in one case (FIG. 10A), a coil, and in other cases, a hollow cup or a flat sheet with surface grid patterns (FIG. 10B). The $T_g$'s of the hybrid SMP, as determined by differential scanning calorimetry (DSC), are close to body temperature and can be fine-tuned by manipulating the grafted PLA chain lengths. The $T_g$'s ranged from 42.8° C. to 48.4° C. with the PLA segment grew from 10 to 40 repeating units (FIG. 7D). The storage and flexural moduli of the SMP are in the GPa range at both room temperature and body temperature, close to those exhibited by human cortical bone. The moduli of the SMP are tunable by PLA chain lengths and decreased with increasing temperature (FIG. 7E-7I).

Example III

Demonstration of the Temporary Shape Fixation Stability and Shape Recovery Efficiency of Urethane-Crosslinked POSS-(PLA$_n$)$_8$

Bulk urethane-crosslinked POSS-(PLA$_n$)$_8$ with varying permanent shapes, sizes and surface patterns can be fabricated using the solution casting method. Examples of the bulk materials with pre-programmed permanent shapes are shown in FIGS. 10A and 10B. These materials can be deformed into any desired temporary shapes or surface patterns beyond their glass transition temperatures, and can be held stably at these temporary shapes for months to years upon cooling to room temperature, without slowly creeping back to their permanent shapes (FIG. 10B). As soon the thermal stimuli are reapplied, however, these materials instantaneously (~1 sec) returned to their pre-programmed permanent shapes or surface patterns (FIGS. 10A and 10B). Such stable shape fixation at room or body temperatures as well as the high shape recovery efficiency is consistent with the modulus-temperature data shown in FIGS. 7E-7I.

Example IV

Synthetic Modification of POSS-poly(ester-urethane) SMP

In certain embodiments, the applicants can introduce new functionlization sites through the modification of the crosslinker rather than the star-shaped macromer 2. As shown in FIG. 8, one uses azido-isocyanate 3 (route 8A) or alkynyl-isocyanate 4 (route 8B) along with the diisocyanate to crosslink star-shaped macromer 2 to form azido-POSS-poly(ester-urethane) or alkynyl-POSS-poly(ester-urethane), respectively. By keeping the stoichiometric ratio of 3 or 4 to diisocyanate low, one keeps the majority of the eight terminal hydroxyls of 2 crosslinked as usual, thus maintaining its shape memory behavior. One introduces a small amount of azido- or alkynyl-groups to the graft (e.g. by coupling 3 or 4 to one of the terminal hydroxyls of macromer 2 via urethane linkages), and allows the introduction of the RGD peptide, HA-binding peptide or PMA functionalized with the complimentary reactive sites by a coupling reaction between the azido group and the alkyne group. One can carry this reaction out under very mild conditions, and it is tolerant to other functional groups including peptide side chains and polar carboxylates that are richly present in PMA. One couples an alkyne-terminated RGD-containing pentapeptide and an alkyne-terminated 12mer HA-binding peptide to the exposed azido groups of the polymer grafts to generate cell adhesive and/or HA-nucleating SMP (FIG. 8A).

As shown in FIG. 8C, 1 eq. macromer 2, 2 eq. 3-diazopropanol and 5 eq. hexamethylene diisocyanate were mixed in 5 eq. dichloromethane with the addition of 100 ppm dibutyltin dilaurate as the catalyst. The solution was stirred for 2 hour and then poured into Teflon molds to evaporate the solvent at room temperature overnight under nitrogen. The materials were further crosslinked for another 24 h at 75° C. and 48 h at 75° C. under vacuum. The crosslinked material 7 were soaked in chloroform for 12 h to remove any un-reacted monomers and soluble components. The FTIR of crosslinked 7 (FIG. 8D) shows characteristic absorption for the azido functionality (~2200 cm-1).

One can introduce an rhBMP-2-retention domain by the attachment of azido-terminated polymethacrylic acid 6 to the alkynyl-POSS-poly(ester-urethane) SMP (FIG. 8B). One prepares the azido-PMA 6 by reversible addition fragmentation transfer (RAFT) polymerization of methacrylic acid initiated by the azido-RAFT agent 5 as disclosed in Quemener et al., *Chem. Comm.*, 5051-5053 (2006), incorporated herein by reference.

One can further functionalize the shape memory polymer by the attachment of small molecule CTA-1 via acyl chloride intermediate CTA-1b (FIG. 8E) to the hydroxyl termini of macromer 2 to enable subsequent RAFT polymerization. The attachment of CTA-1 to macromer 2 was accomplished in 92% yield (FIG. 8E). Briefly, oxalyl chloride (1.455 g) was reacted with CTA-1 (0.4662 g, 2.078 mmol) under N2 for 2 h at rt and then 3 h at 55° C. The volatile was removed under vacuum before macromer 2 (n=20, Mw/Mn=1.23, 0.5695 g) in 15 mL THF was added. The reaction proceeded at 55° C. for 12 h before the volatile was removed by distillation. The resulting red oil was dissolved in 30 mL ethyl acetate, washed with 100 mL saturated NaHCO3 aq. solution, dried with anhydrous MgSO4, and precipitated in 100 mL hexane. The yellow solid was further purified by dissolving in THF and precipitating in hexane 3 times. Drying under vacuum at 40° C. yielded spectroscopically pure macromer CTA (n=20, 0.5308 g, 92%). 1H NMR (400 MHz, CDCl3): d 5.24-5.12 (172H, br), 5.12-5.05 (8H, q, J=7.0 Hz), 4.10 (16H, t, J=6.6 Hz), 3.27 (16H, q, J=7.4 Hz), 1.74 and 1.70 (48H, s), 1.68-1.49 (560H, br), 0.60 (16H, t, J=8.6 Hz), 0.16-0.05 (48H, s) ppm. 13C NMR (100 MHz, CDCl3): d 221.44, 172.22, 170.23-169.28, 69.52-68.89, 67.78, 55.71, 31.29, 25.39 and 25.13, 22.26, 16.96-16.76, 13.47, 13.04, −0.32 ppm. GPC characterization using two 5-mm PLGel MiniMIX-D columns confirmed that narrow molecular weight distribution of macromer 2 (PDI=1.23, red trace, FIG. 10) was retained upon attachment of the CTA (PDI=1.22, green trace, FIG. 8F).

The efficiency for macromer CTA to initiate RAFT was illustrated by grafting 200 repeating HEMA units to each arm of the macromer. A 5-mL N,N-dimethylformamide (DMF) solution of macromer CTA (n=20, PDI=1.22, 161.0 mg, 0.01 mM), AIBN (3.3 mg, 0.02 mM), and HEMA (2.080 g, 16.0 mM) was placed in a 25-mL Schlenc flask, degassed with 3 freeze-evacuate-thaw cycles, and reacted at 65° C. under N2 for 10 h. The reaction mixture was precipitated in cold ethyl ether to yield yellow solid, which was further purified by precipitation in DMF/ethyl ether 3 times to give POSS-(PLA20-co-pHEMA200)$_8$ (1.3 g, 65%). GPC characterization revealed a narrow molecular weight distribution (PDI=1.34, blue trace, FIG. 8F), indicating the achievement of a well-controlled RAFT initiated by the macromer CTA. 1H NMR integration suggested a 222,000 molecular weight for POSS-(PLA20-co-pHEMA200)$_8$, confirming an average of 200 repeating HEMA units in each grafted pHEMA arm. 1H NMR (400 MHz, CD3OD): d 5.20 (260H, br), 4.04 (5505H, br), 3.78 (5505H, br), 2.17-1.87 (5505H, br), 1.62-1.49 (780H, br), 1.32 (330H, br), 1.17 and 0.94 (8041H, br), 0.21 (48H, br) ppm. As expected, the integrations for the proton signals corresponding to the inner core structure of the macromer were lower than theoretical values due to the limited motion of the core in the NMR solvent.

Example V

In Vitro Bioactivities of the SMP Bone Grafts

One may determine the HA-nucleating capacity induced by the HA-binding peptide attached to the SMP graft in vitro by the method disclosed herein or as appropriately modified. One soaks a graft in a HA-mineralization solution consisting of 5 mM $Na_2HPO_4$ and 10 mM $CaCl_2$ precursor ions. One retrieves the grafts after being incubated at 37° C. for 2, 12, 24 and 48 h. One washes and freeze-dries the retrieved grafts for scanning and transmission electron microscopy analyses. One examines the morphology and crystallinity of the templated HA-mineral growth on both the surface and at the cross-section of the graft.

One examines the role of the GRGDS peptide functionalized on the SMP graft in promoting cell attachment by comparing the rate of cell attachment, the morphology, and the spreading of the attached cells in the early culture (2, 4, 12 and 24 hours) of mouse osteoblast-like MC3T3-E1 cells on crosslinked POSS-poly(ester-urethane) 2 vs. on crosslinked cell adhesive POSS-poly(ester-urethane) substrates. Fast attachment and good spreading of MC3T3-E1 indicates good initial cell-material interactions.

One determines the biological activity of rhBMP-2 pre-absorbed to and released from the SMP graft functionalized with the PMA domains by testing its ability to convert the differentiation pathway of mouse C2C12 myoblasts (which have zero/low endogenous background of BMP-2) into the osteoblast lineage. One plates C2C12 cells in low mitogen medium (5% FBS). One adds, the graft (5×5×1 mm) pre-absorbed with rhBMP-2 (0-0.5 µg/graft) to the culture. One adds an appropriate dose of BMP-2 (300 ng/mL) for converting C2C12 into osteoblast lineage to a positive control culture. At 2 and 4 days, one fixes the cell layers with 2% paraformaldehyde and stains for alkaline phosphatase (ALP), a marker for osteoblast differentiation, following standard protocol. Positive ALP staining indicates osteoblast differentiation.

Example VI

Angioplasty of an Arthoscloritic Plaque

One molds the materials disclosed in Examples 2 and 3 into a tubular web stent. The stent is coated with a material that degrades artherosclerotic plague a described in U.S. Pat. No. 7,195,640. One places the stent into a position in the cardiovascular system subject to atherosclerosis. The stent shape expands upon exposure to body temperature and degrades over time.

Example VII

In Vitro Hydrolytic Degradation of Urethane-Crosslinked POSS-(PLA$_n$)$_8$ SMP

The hydrolytic degradation of urethane-crosslinked macromer 2 was examined in PBS (pH 7.4) at 37° C. over a course of 9 months. The extent of degradation as a function of PLA chain lengths was monitored as the weight loss of the material over time (FIG. 12A). As expected, the crosslinked macromers with shorter PLA (n=10, 20) led to faster degradation, losing >50% of mass in 3 months, whereas significant mass reduction was not detected with that containing longer PLA (n=40) until after 6 months. SEM micrographs (FIGS. 12B-G) confirmed that the material containing shorter PLA (n=10, 20) degraded to generate high porosity by day 73 whereas little degradation was detected for the one with longer PLA (n=40). The tunable degradation rate matching with normal fracture healing and spine fusion rate (2-6 months) combined with the tunable cortical bone-like mechanical properties of the crosslinked macromers support the notion that the shape memory polymer can be engineered for orthopedic applications.

Example VIII

In Vivo Evaluation of POSS-PLA Macromers

Figure 13:
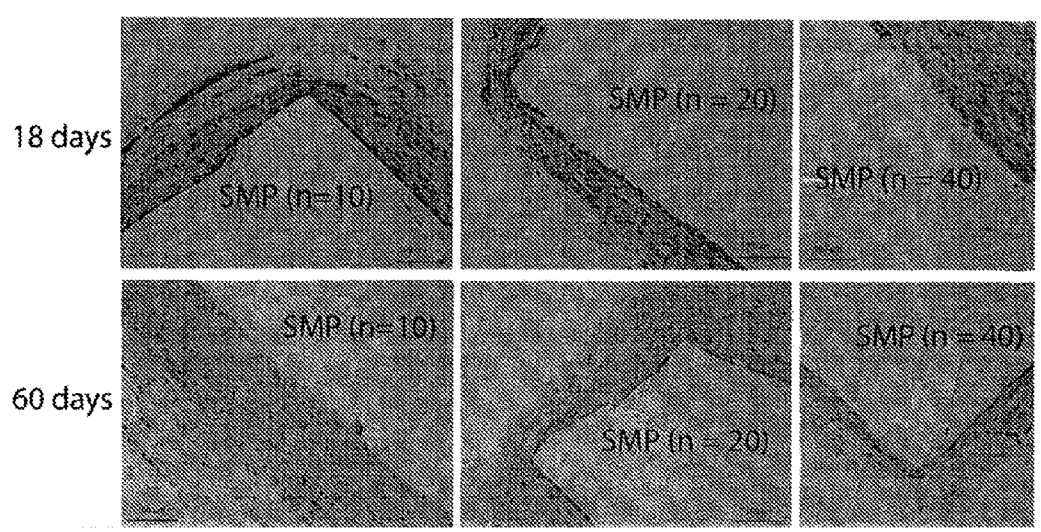
FIG. 13 shows images of the retrieved urethane-crosslinked POSS-(PLA)$_n$ (n=10, 20, 40) after 18-60 days of subcutaneous implantation under the rib cage of rats. All sections are 6 μm in thickness, and stained by hematoxylin and eosin. Double arrows indicate normal fibrous tissue encapsulation of the implants.

As an example of one utility of the present invention, we evaluated the in vivo implantation of the shape memory polymer containing the urethane-crosslinked POSS-PLA motifs into a mammalian subject. As shown in FIG. 13, subcutaneous implantation of urethane-crosslinked (POSS-PLA$_n$)$_8$ (n=10, 20, 40) under the rib cage in rats led to negligible inflammatory response, suggesting excellent biocompatibility of the shape memory polymers. All sections shown are 6 µm in thickness, and stained by hematoxylin and eosin. Normal fibrous tissue encapsulation (indicated by double arrows) were observed in all cases. These results are suggestive of the efficacy of the present invention in biomaterials compatible with the natural tissue environment as well as biomaterials that are resistant to, e.g., immunological rejection.

Example IX

Preparation of Porous Urethane-Crosslinked POSS-(PLA$_n$)$_8$ and its Retained Thermal Responsive Shape Memory Behavior Macroporous urethane-crosslinked POSS-(PLA$_n$)$_8$ scaffold can be fabricated by many methods including salt-leaching, porogen leaching, thermally induced phase separation, and solid freeform fabrication techniques, etc. The porous scaffold shown in FIG. 14 was prepared by the salt-leaching method. Briefly, the shape memory polymer crosslinking components (1 eq POSS-(PLA)$_{20}$, 4 eq hexamethylenediisocyanate, and 100 ppm dibutyltin dilaurate) were stirred in 2.5 times (w/w) CH$_2$Cl$_2$ at room temperature for 2 hours, before sodium chloride salt (70% w/w) was added and mixed thoroughly while the solvent was being evaporated under nitrogen. The mixture was left under nitrogen atmosphere overnight at room temperature before it was further crosslinked at 75° C. under nitrogen for 24 hours and at 75° C. under vacuum for 48 hours to remove any residual volatiles. The sodium chloride salt was removed by washing the composite in water under stirring for 24 hours. The scaffold was then freeze dried for 24 hours.

Figure 14:
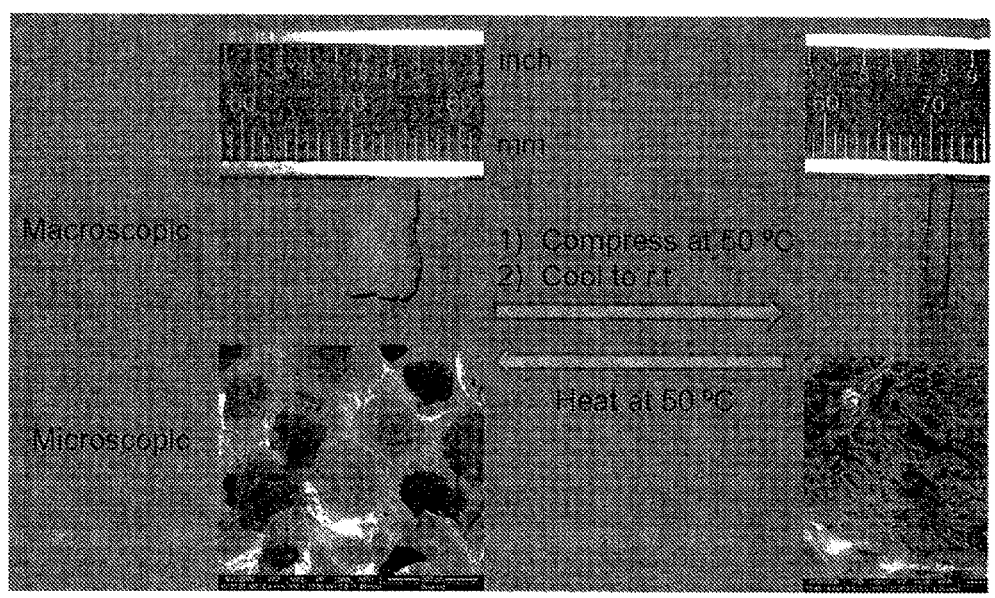
FIG. 14 shows a sample of a porous shape memory polymer collapsed under compression and reopened upon thermal stimulation, both macroscopically and microscopically as indicated by the scanning electron microscopy (SEM) image.

As shown in FIG. 14, the porous bulk material prepared using this method retained the thermal responsive shape memory behavior as illustrated by the collapse of the pores upon compression at 50° C., and the subsequent re-opening of the collapsed pores when the 50° C. thermal stimulation is reapplied to the compressed material. Such behavior is supported by the evidence of both thermal responsive macroscopic shape change and microscopic pore recovery as shown by the scanning electron micrographs (FIG. 14).

Example X

Preparation of Urethane-Crosslinked POSS-(PLA$_n$)$_8$/ Tricalcium Phosphate (TCP) Composite A varying content of inorganic minerals can be incorporated with the shape memory polymer to fabricate composite material. For instance, the shape memory polymer crosslinking components (1 eq POSS-(PLA)$_{20}$, 4 eq hexamethylenediisocyanate, and 100 ppm dibutyltin dilaurate) were stirred in 2.5 times (w/w) CH$_2$Cl$_2$ at room temperature for 2 hours, before tricalcium phosphate (50% w/w) was added and mixed thoroughly while the solvent was being evaporated under nitrogen. The mixture was left under nitrogen atmosphere overnight at room temperature before it was further crosslinked at 75° C. under nitrogen for 24 h and at 75° C. under vacuum for 48 hours to remove any residual volatiles. The resulting dense composite was obtained with excellent structural integration between the biomineral and the polymer matrix.

We claim:

1. A composition comprising:
   a) a core comprising siloxane moieties;
   b) at least three polymers grafted to said siloxane moieties to form a plurality of siloxane-polymer conjugates, wherein each of the said at least three polymers comprises at least two reactive functional groups selected from the group consisting of an ester group, an alkenyl group, a hydroxyl group, an amide group, and a carboxylic acid group;
   c) a crosslinked network formed by linking groups joining two or more of said siloxane-polymer conjugates, wherein
      said siloxane moieties are caged structures,
      said linking groups are selected from the group consisting of alkyl, aryl, polyethylene and urethane groups, and
      said composition has a T$_g$ between 17° C. and 100° C.

2. The composition of claim 1, wherein at least one of said at least three polymers is a polyester.

3. The composition of claim 1, wherein said siloxane moieties are selected from the group consisting of silsesquioxanes and metallasiloxanes.

4. The composition of claim 3, wherein said siloxane moieties are silsesquioxanes.

5. The composition of claim 1, wherein said siloxane moieties are metallasiloxanes.

6. The composition of claim 5, wherein said linking groups comprise aryl groups.

7. The composition of claim 5, wherein said linking groups comprise alkyl groups.

8. The composition of claim 5, wherein said linking groups comprise polyethylene groups.

9. The composition of claim 5, wherein said linking groups comprises urethane groups.

10. The composition of claim 5, wherein at least one of said at least three polymers is a polyester.

11. The composition of claim 5, wherein said composition has one-way or two-way shape memory.

12. A method of supplementing or repairing a bone in a subject comprising:
    1) providing
       a) said composition of claim 1, and
       b) a subject suspected of or exhibiting symptoms associated with a bone disorder or dysfunction; and
    2) administering said composition to said subject under conditions such said symptoms are reduced.

13. The method of claim 12, wherein said mode of administration is surgical implantation.

14. The method of claim 12, wherein the bone exhibiting said bone disorder or dysfunction is selected from the group consisting of cranial bones, mandible, ulna, humerus, radius, vertebrae, carpals, metacarpals, phalanges, ilium, ischium, pubis, femur, hip joint, patella, tibia, fibula, tarsals and metatarsals.

15. The method of claim 12, wherein said bone disorder or dysfunction is selected from the group consisting of bone fracture, bone cyst, bone spur, bone tumor, craniosynostosis, fibrodysplasia ossificans progressiva, fibrous dysplasia, giant cell tumor of bone, hypophosphatasia, Klippel-Feil syndrome, metabolic bone disease, osteitis deformans, osteitis fibrosa cystica, osteitis pubis, condensing osteitis, osteitis condensans ilii, osteochondritis dissecans, osteochondroma, osteogenesis imperfecta, osteomalacia, osteomyelitis, osteopenia, osteopetrosis, osteoporosis, osteosarcoma, porotic hyperostosis, primary hyperparathyroidism and renal osteodystrophy.

16. The method of claim 12, wherein said subject is a mammal.

17. The method of claim 12, wherein at least one of said at least three polymers is a polyester.

18. The method of claim 12, wherein said siloxane moieties are selected from the group consisting of silsesquioxanes and metallasiloxanes.

19. The method of claim 18, wherein said siloxane moieties are silsesquioxanes.

20. The method of claim 18, wherein said siloxane moieties are metallasiloxanes.

* * * * *